(12) United States Patent
Ferris et al.

(10) Patent No.: US 6,711,430 B1
(45) Date of Patent: Mar. 23, 2004

(54) METHOD AND APPARATUS FOR PERFORMING NEUROIMAGING

(75) Inventors: Craig F. Ferris, Holden, MA (US); Jean A King, Worcester, MA (US); Arthur C. Allard, Templeton, MA (US); Reinhold Ludwig, Paxton, MA (US); Gene Bogdanov, Manchester, CT (US)

(73) Assignee: Insight Neuroimaging Systems, Inc., Worcester, MA (US)

( * ) Notice: Subject to any disclaimer, the term of this patent is extended or adjusted under 35 U.S.C. 154(b) by 0 days.

(21) Appl. No.: 09/694,087

(22) Filed: Oct. 20, 2000

Related U.S. Application Data

(63) Continuation-in-part of application No. 09/169,602, filed on Oct. 9, 1998, now Pat. No. 6,275,723.

(51) Int. Cl.⁷ .............................. A61B 5/055; G01V 3/00
(52) U.S. Cl. ..................... 600/417; 600/422; 324/318
(58) Field of Search ................................ 600/415, 417, 600/421, 422; 324/318, 322; 606/130

(56) References Cited

U.S. PATENT DOCUMENTS

| | | |
|---|---|---|
| 1,093,112 A | 4/1914 | Clarke et al. |
| 4,256,112 A | 3/1981 | Kopf et al. |
| 4,534,050 A | 8/1985 | Smith |
| 4,602,622 A | 7/1986 | Bar et al. |
| 4,617,925 A | 10/1986 | Laitinen |
| 4,634,980 A | 1/1987 | Misic et al. |
| 4,638,798 A | 1/1987 | Shelden et al. |
| 4,812,761 A | 3/1989 | Vaughan, Jr. |
| 5,154,723 A | 10/1992 | Kubota et al. |
| 5,281,232 A | 1/1994 | Hamilton et al. |
| 5,304,933 A * | 4/1994 | Vavrek et al. ............... 324/318 |
| 5,311,868 A | 5/1994 | Carbini et al. |
| 5,311,882 A | 5/1994 | Gagne |
| 5,330,485 A | 7/1994 | Clayman et al. |
| 5,370,117 A | 12/1994 | McLaurin, Jr. |
| 5,388,580 A | 2/1995 | Sullivan et al. |
| 5,400,787 A | 3/1995 | Marandos ................. 128/653.5 |
| 5,531,229 A | 7/1996 | Dean et al. |
| 5,577,503 A | 11/1996 | Bonutti |

(List continued on next page.)

FOREIGN PATENT DOCUMENTS

| | | | |
|---|---|---|---|
| DE | 44 08 194 | 9/1995 | ........... G01R/33/30 |
| EP | 0290187 | 11/1988 | ........... G01N/24/04 |
| WO | 00/57782 | 10/2000 | ........... A61B/5/055 |

OTHER PUBLICATIONS

K. Kamada et al., "Anatomical and functional imaging of the auditory cortex in awake mustached bats using magnetic resonance technology" Brain Research Protocols, vol. 4, 1999, pp. 351–359.

K. Lahti et al., "Imaging brain activity in conscious animals using functional MRI" Journal of Neuroscience Methods, vol. 82, No. 1, Jul. 1, 1998, pp. 75–83.

T. Kamiryo, et al., "Enhanced Magnetic Resonance Imaging of the Rat Brain Using a Stereotactic Device with a Small Head Coil: Technical Note", *Act Neurochir* 133:87–92 (1995).

E. Tabuchi, et al., "Functional MRI Using Awake Animal: Brain Activity Induced by Drinking", *Jpn. J. Physiol* 45(1):S194 (1995).

*Primary Examiner*—Shawna J. Shaw
(74) *Attorney, Agent, or Firm*—Darby & Darby

(57) ABSTRACT

The present invention relates to systems and methods of performing magnetic resonance imaging (MRI) in awake animals. The invention utilizes head and body restrainers to position an awake animal relative to a radio frequency dual coil system operating in a high field magnetic resonance imaging system to provide images of high resolution without motion artifact.

31 Claims, 32 Drawing Sheets

U.S. PATENT DOCUMENTS

| | | |
|---|---|---|
| 5,588,430 A | 12/1996 | Bova et al. |
| 5,595,191 A | 1/1997 | Kirk |
| 5,601,570 A | 2/1997 | Altmann et al. |
| 5,640,958 A | 6/1997 | Bonutti |
| 5,646,530 A | 7/1997 | Strenk et al. ............... 324/318 |
| 5,681,326 A | 10/1997 | Lax |
| 5,736,858 A * | 4/1998 | Katznelson et al. ........ 324/318 |
| 5,738,045 A | 4/1998 | Bleacher |
| 5,744,957 A | 4/1998 | Vaughan, Jr. |
| 5,751,146 A | 5/1998 | Hrovat |
| 5,782,765 A | 7/1998 | Jonkman |
| 5,797,924 A | 8/1998 | Schulte et al. |
| 5,800,353 A | 9/1998 | McLaurin, Jr. |
| 5,836,878 A | 11/1998 | Mock et al. |
| 5,887,074 A | 3/1999 | Lai et al. |
| 5,898,306 A * | 4/1999 | Liu et al. .................... 324/322 |
| 5,917,324 A | 6/1999 | Leussler .................... 324/318 |
| 6,138,302 A | 10/2000 | Sashin et al. |
| 6,232,779 B1 * | 5/2001 | Tropp et al. ................ 324/322 |
| 6,275,723 B1 * | 8/2001 | Ferris et al. ................ 600/417 |

* cited by examiner

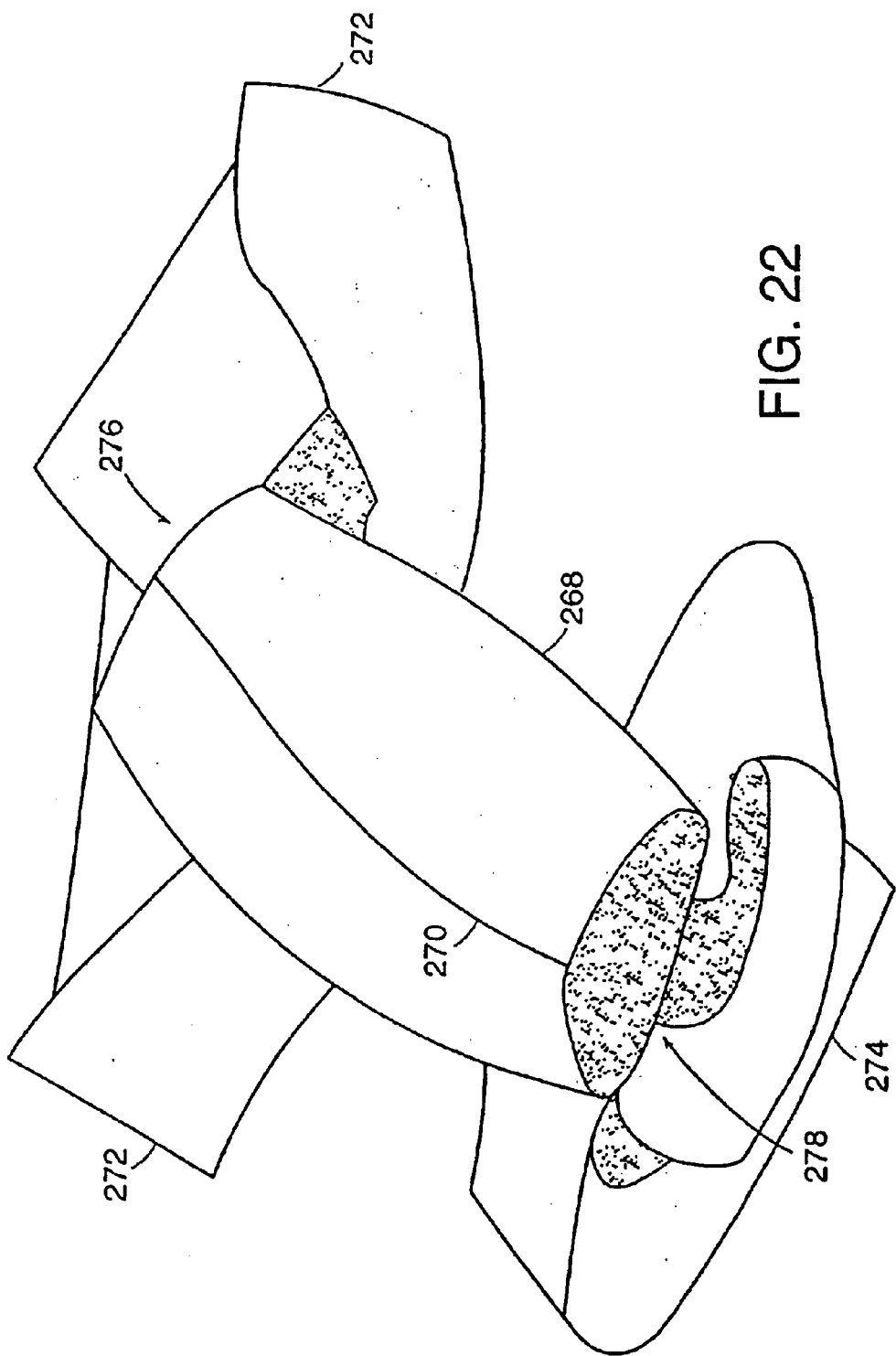

Pre Stroke        60 min Post Stroke

METHOD AND APPARATUS FOR PERFORMING NEUROIMAGING

RELATED APPLICATION(S)

This application is a is a continuation-in-part of U.S. application Ser. No. 09/169,602 filed on Oct. 9, 1998 now U.S. Pat. No. 6,275,723 issued Aug. 14, 2001, the entire teachings of which are incorporated herein by reference.

GOVERNMENT SUPPORT

The invention was supported, in whole or in part, by a grant R42MH59501 from National Institutes for Health. The Government has certain rights in the invention.

BACKGROUND OF THE INVENTION

The present invention relates to magnetic resonance imaging, and more particularly to a method and apparatus for performing functional magnetic resonance imaging (fMRI) in conscious animals.

Human studies utilizing fMRI have advanced our understanding of the regional and functional interplay between populations of neurons serving sensory, integrative and motor functions. Changes in neuronal activity are accompanied by specific changes in hemodynamics such as cerebral blood flow, cerebral blood volume, and blood oxygenation. Functional MRI has been used to detect these changes in response to visual stimulation, somatosensory activation, motor tasks, and emotional and cognitive activity. When the brain is activated by any of these conditions, the blood flow and delivery of oxygen to the active regions the tissue oxygen uptake resulting in an increase in blood oxy-hemoglobin ($HbO_2$) content. The susceptibility difference between diamagnetic oxy-hemoglobin and paramagnetic deoxy-hemoglobin (Hb) creates local magnetic field distortions that affect the processional frequency of the water protons. The consequential change in magnetic resonance (MR) signal intensity which is proportional to the ratio of $HbO_2$ to Hb. These signal-intensity alterations related to blood oxygenation are termed the BOLD (blood oxygenation-level-dependent) effect. The voxels in paramagnetic Hb content is decreased are illuminated in the image.

While most work on fMRI has been done in humans, it has been difficult to use this technology in conscious animals because of motion artifact. As a result, most studies to date have been limited to animals which are typically anesthetized in order to minimize this problem of motion artifacts. The low level of arousal during anesthesia either partially or completely suppresses the fMRI response and has impeded fMRI application to the more physiologically relevant functions that have been noted in humans.

Since image resolution is a salient feature of fMRI, precautions to ensure improved image quality with minimized head movements are essential. In addition to head movement, it has been observed that any motion outside the field of view can obscure or mimic changes in signal.

Another, equally significant component for achieving high temporal and spatial image resolution is the generation of radiofrequency (RF) magnetic fields. The RF field pulses are transmitted to flip protons into the transverse plane of the main direct current (DC) magnetic field. As these protons precess and relax back into the longitudinal plane of the main magnetic field they emit RF magnetic field signals. The electrical assemblies capable of sending and receiving RF signals are called RF probes, coils, or resonators. Ideally, a RF coil used for magnetic field transmission creates a large homogenous area of proton activation at a very narrow bandwidth center around the proton resonance frequency with minimal power requirements. An RF coil used for receiving covers the largest region of interest within the sample at the highest signal-to-noise ratio (SNR). RF coils are either volume coils or surface coils. A volume coil has the advantage of both sending and receiving RF signals from large areas of the sample. However, signal-to-noise ratio is compromised because a large spatial domain contributes to the RF signal, resulting in additional noise and thereby obscuring the RF signal from the region of interest. A surface coil has the advantage of improved SNR due to its close proximity to the sample. Unfortunately, a surface coil is ill suited for RF energy transmission owing to the fact that only a small proton area can be activated. Two criteria are sought in the design of superior coil performance for high field animal studies. First, the coils must be as efficient as possible. Transmission efficiency is increased by reducing the resistive coil losses through appropriate arrangement of conductors, the use of a shield, and the employment of low loss dialectric materials. By using a separate surface coil in proximity over the desired field of view (FOV) or region of interest, the reception efficiency of the acquired NMR signal is further increased. In imaging, spatial and temporal resolutions are proportional to SNR.

The second criterion to be met for a volume coil, is the uniformity or homogeneity over a desired FOV in the animal sample. To achieve both homogeneity and efficiency for volume coils of Larmor wavelength dimensions, further improvements are required. Conventional state-of-the-art birdcage coil designs will not resonate at these dimensions.

So-called transversal electromagnetic (TEM) resonator designs have shown promise for high-frequency, large volume coil applications for humans. However, these TEM designs must be improved upon for the highest frequency and animal applications allowed by present and future magnets, e.g; for the 9.4T, and the 11.74T, magnets presently being built for laboratory animal studies.

Increased SNR is sought by making NMR measurements at higher magnetic, or Bo, fields. Main magnetic field strength is, however, only one of several parameters affecting the MR sensitivity. RF coil and tissue losses can significantly limit the potential SNR gains realized at high fields. SNR (and reciprocal transmission efficiency) will suffer when the coil's ohmic resistance, radiation resistance, coupled issue losses, RF magnetic field and angular frequency are not optimized.

Tissue losses increasingly impact SNR at higher frequencies. These conductive and dielectric losses represented are limited in practice by using local surface coils, or volume coils efficiently coupled to a region of interest. In addition to tissue loading, RF losses in the coils themselves become significant at higher frequencies. The RF coil loss increases with frequency as do the resistive losses in the coil RC, which increases with the square root of the angular frequency, and the losses from radiation resistance, which increases as at the fourth power of the angular frequency. The radiation losses also increase as the coil size increases as $S^2$, where S is the area bounded by the coil.

From the above, it is apparent that radiative losses to the sample and environment, as well as conductive losses to the load of a coil become severe to the point of limiting and eventually degrading the SNR gains otherwise expected at higher magnetic field strengths. Physically, as a coil is increased in dimension and/or frequency, its electrical circuit length increases, the coil ceases to behave like a "coil" (RF field storage circuit) and begins to behave more like an "antenna" (RF field energy radiator).

SUMMARY OF THE INVENTION

Applicant's method and apparatus overcomes the difficulties of performing fMRI on conscious animals by utilizing a restraining assembly to eliminate movement artifacts in combination with RF resonator system to enhance MR signal for mapping changes in brain activity. The restraining assembly incorporates a coil design including a spatially adjustable volume coil for transmitting RF magnetic field pulses and a spatially adjustable dome shaped surface coil for receiving the RF response signals from the conscious animal. The significance of applicant's method of neuroimaging in conscious animals will change current imagery of the brain from either a static (as seen with most neurochemical measurements) or a low activation dynamic system in an anesthetized state (as seen with current fMRI or positron emission tomography (PET) measurements) to more physiologically relevant conditions.

There are two approaches to remedy the problem of high-frequency radiative losses: 1) construct smaller coils or array elements; and 2) build coils by transmission line or transverse electromagnetic (TEM) principles. Transmission lines eliminate radiative loss. Often it is desirable to transmit with a larger homogeneous TEM volume coil and receive with a smaller, closer fitting surface coil. However, to operate a transmitting TEM volume coil in conjunction with a receiving surface coil, or an array surface coil, involves switching circuits and an active tuning/detuning methodology. Thus, the present invention employs a coil mounted on a restraining assembly.

A preferred embodiment of the present invention immobilizes the head and body of conscious animals for several hours, without compromising physiological functions. The apparatus allows for collection of a consistent voxel by voxel representation of the brain over several data acquisitions under various experimental conditions. Applicants have demonstrated fMRI signal changes with high temporal and spatial resolution in discrete brain areas in response to electrical stimulation, such as footshock and during odor stimulation. Changes are measured in conscious animals with and without the use of contrast agents. Importantly, the information is obtained without injury to the animal and provides a method of performing developmental measurements on the subject over the course of its life.

The single or multi-cylindrical non-magnetic restraining assembly immobilizes the head and body of conscious animals for insertion into the bore of a magnetic resonance (MR) spectrometer.

A restraining assembly according to the invention for imaging conscious animals includes a head restrainer that restrains the head of the conscious animal, a body restrainer that restrains the body of the animal, and a frame on which the volume coil is mounted. The frame carries both the head restrainer and the body restrainer and has a damping structure for reducing transmission of movement from the body restrainer to the head restrainer.

In an embodiment of the invention, the multi-cylindrical non-magnetic dual-coil animal restrainer to immobilize the head and body of a conscious animal has a cylindrical body restrainer, and a cylindrical head restrainer that are concentrically mounted within the frame.

The frame can also include an adapter to slide into the bore of the MR spectrometer and adjust the diameter of the frame to the inner diameter of the bore. The frame unit includes a first front-end mounting plate having an access hole extending through the plate, a second or rear-end mounting plate parallel and spaced from the front-end mounting plate and having an access hole extending through the second plate, and a plurality of support members or rods extending between the mounting plates to space and support the mounting plates in relative position, wherein the support rods reduce transmission of movement of the body restrainer to the head restrainer, thereby decoupling vibration between the mounting plates. The support rods also act as rails for sliding and positioning the cylindrical volume coil over the head and body restrainers.

The body restrainer holds the body of the conscious animal. The body restrainer can include an elongated cylindrical body tube carried by the frame and a shoulder restrainer carried by the cylindrical body tube that positions of the animal's shoulders once the head restrainer is secured into the front-end mounting plate. The front of the body tube fits into a ring on the backside of the front-end mounting plate. The seal between the front of the body tube and the ring on the front-end mounting plate is cushioned by a rubber gasket to decouple vibration between the body restrainer and the head restrainer.

The head restrainer immobilizes the head of the conscious animal. The head restrainer includes a cylindrical head holder having a bore to receive and restrain the head of an animal, and a docking post at the front of the head restrainer for securing the head holder to the front-end mounting plate.

The head holder restrains the head of the animal to prohibit vertical and horizontal movement of the animal during imaging. The head holder has a bite bar extending horizontally creating a chord along the bottom of its circular aperture. A vertical nose clamp extends through the top of the head holder and abuts the animal's nose to clamp the animal's mouth thereon.

The animal's head is further restrained by a pair of lateral ear clamping elements or screws that extend horizontally through bilateral openings or the sides of the head holder and a nose clamp that extends vertically through the head holder. A protective ear piece is placed over the animal's ears and receives the tips of the lateral ear clamping screws.

A further adaptation of an embodiment includes a restraining jacket to restraining an animal and prohibit limb movement. An animal is placed into the restraining jacket. Holders for the arms and legs may be used to further restrict the animal's movement.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 is a top view of a body tube of the body restraining unit;

FIG. 22 is a view of the restraining jacket;

DETAILED DESCRIPTION OF THE INVENTION

Figure 1:
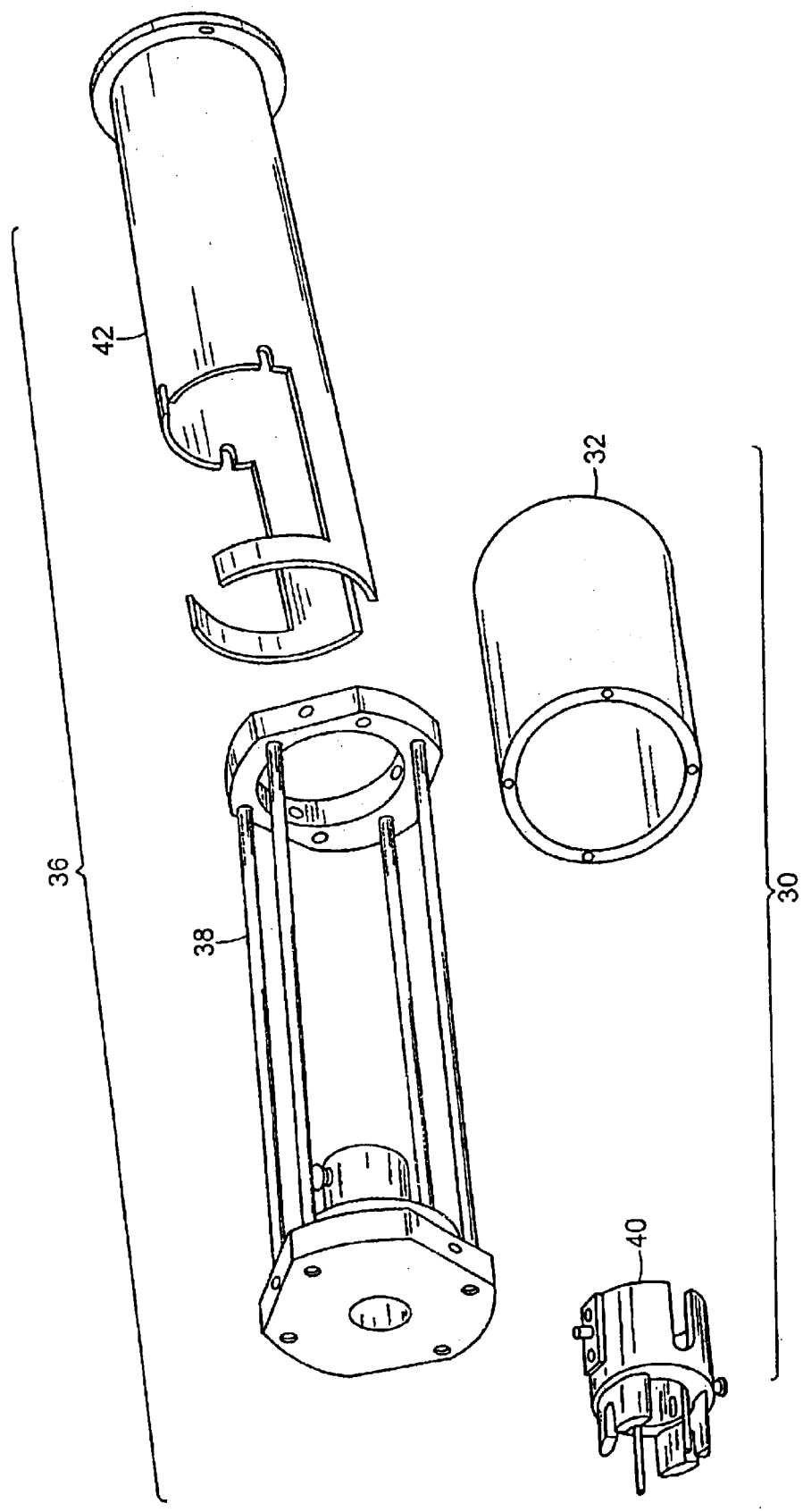
FIG. 1 is a side perspective of a multi-cylindrical non-magnetic dual coil restraint system.
Figure 9:
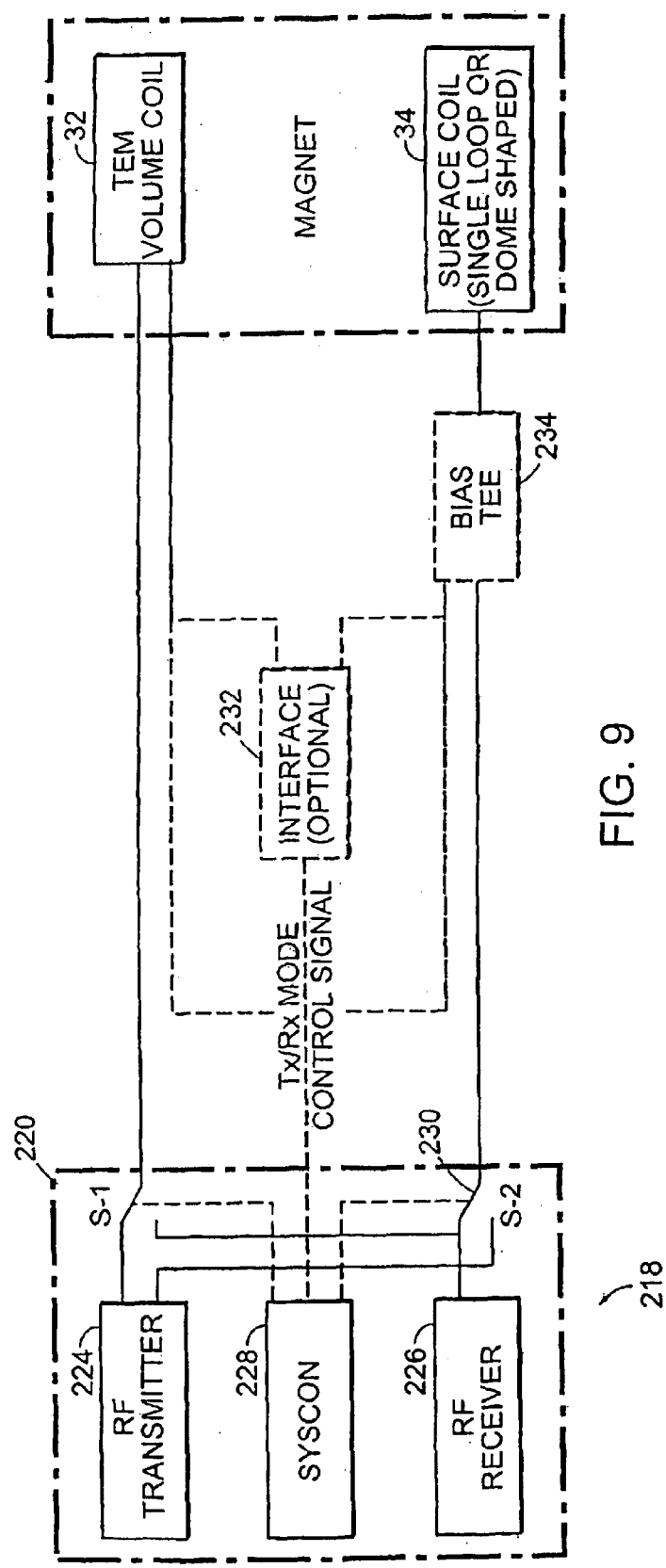
FIG. 9 is a schematic of the interface between the RF-coils and MRI transmit/receive system.

In the figures, like numbers are used to indicate like elements. FIG. 1 shows a multi-cylindrical, dual-coil animal restrainer 30 according to the invention. The multi-cylindrical, dual-coil animal restrainer 30 including a volume coil 32 and a surface coil 34, as seen in FIG. 9, and the method described allow the functional magnetic resonance imaging (fMRI) of conscious animals.

Referring to FIG. 1, the multi-cylindrical, dual-coil animal restrainer 30 has the volume coil 32, which will be described further below in greater detail, and a restraining assembly 36. The restraining assembly 36 includes a support frame or chassis 38, a head retainer 40, and a body retainer 42.

Figure 2:
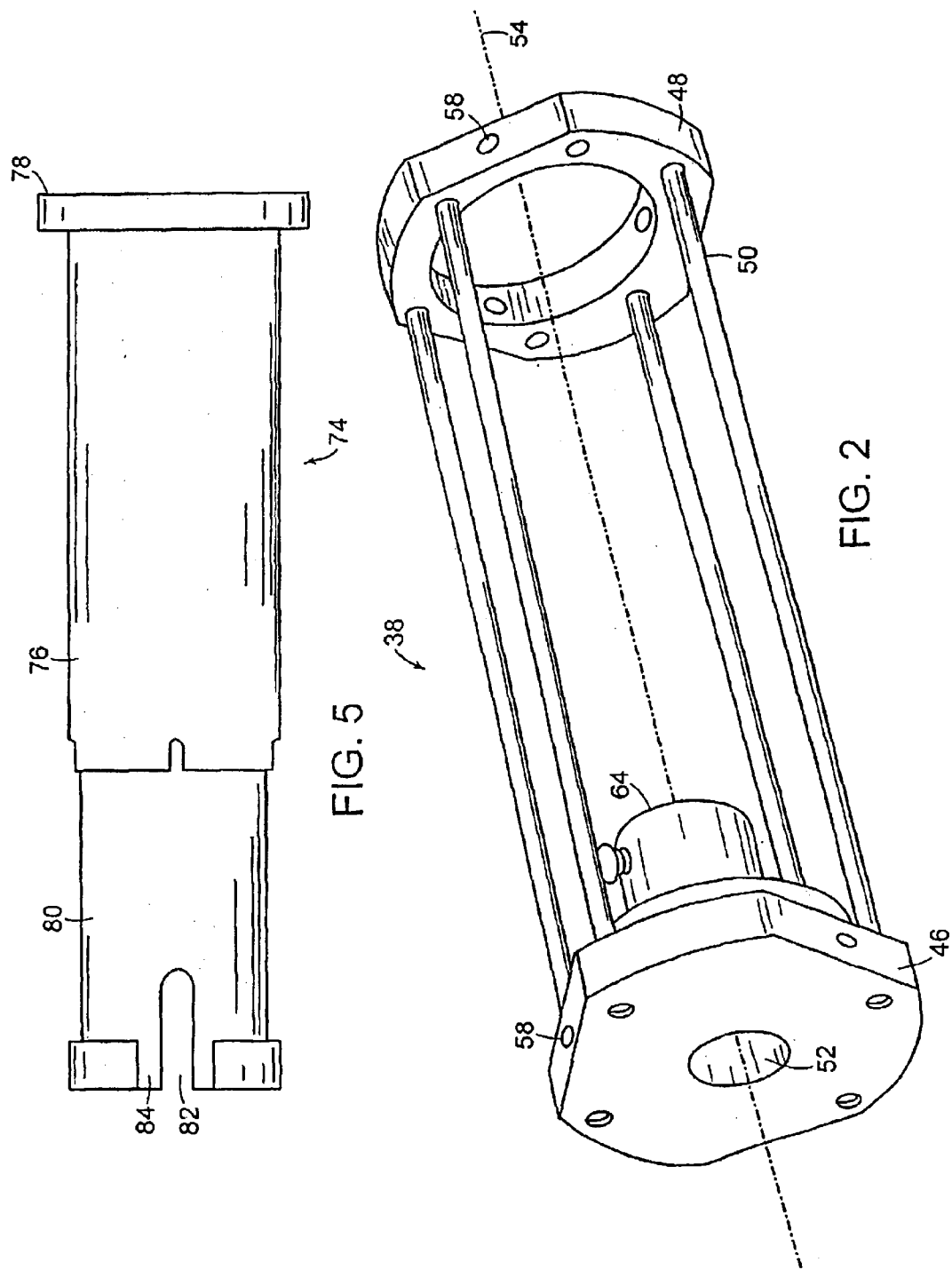
FIG. 2 is a side perspective view of the chassis unit.

The frame 38 is shown in perspective in FIG. 2. The frame 38 has a first or front-end mounting plate 46 and a second or rear-end mounting plate 48 spaced apart by a plurality of support members or rods 50. The front-end mounting plate 46 has a hole 52 which is collinear with a longitudinal axis 54 of the frame 38. The rear-end mounting plate 48 also has a cylindrical opening 56 which is collinear with the longitudinal axis 54. The cylindrical opening 56 of rear-end mounting plate 48 is larger than the hole 52 on the front-end mounting plate for the reasons set forth below. In addition, both the mounting plates 46 and 48 have threaded openings 58 which can receive an adjustable fastening post for centering and securing the frame 38 within a cavity or bore of a magnetic resonance MR spectrometer.

Figure 8:
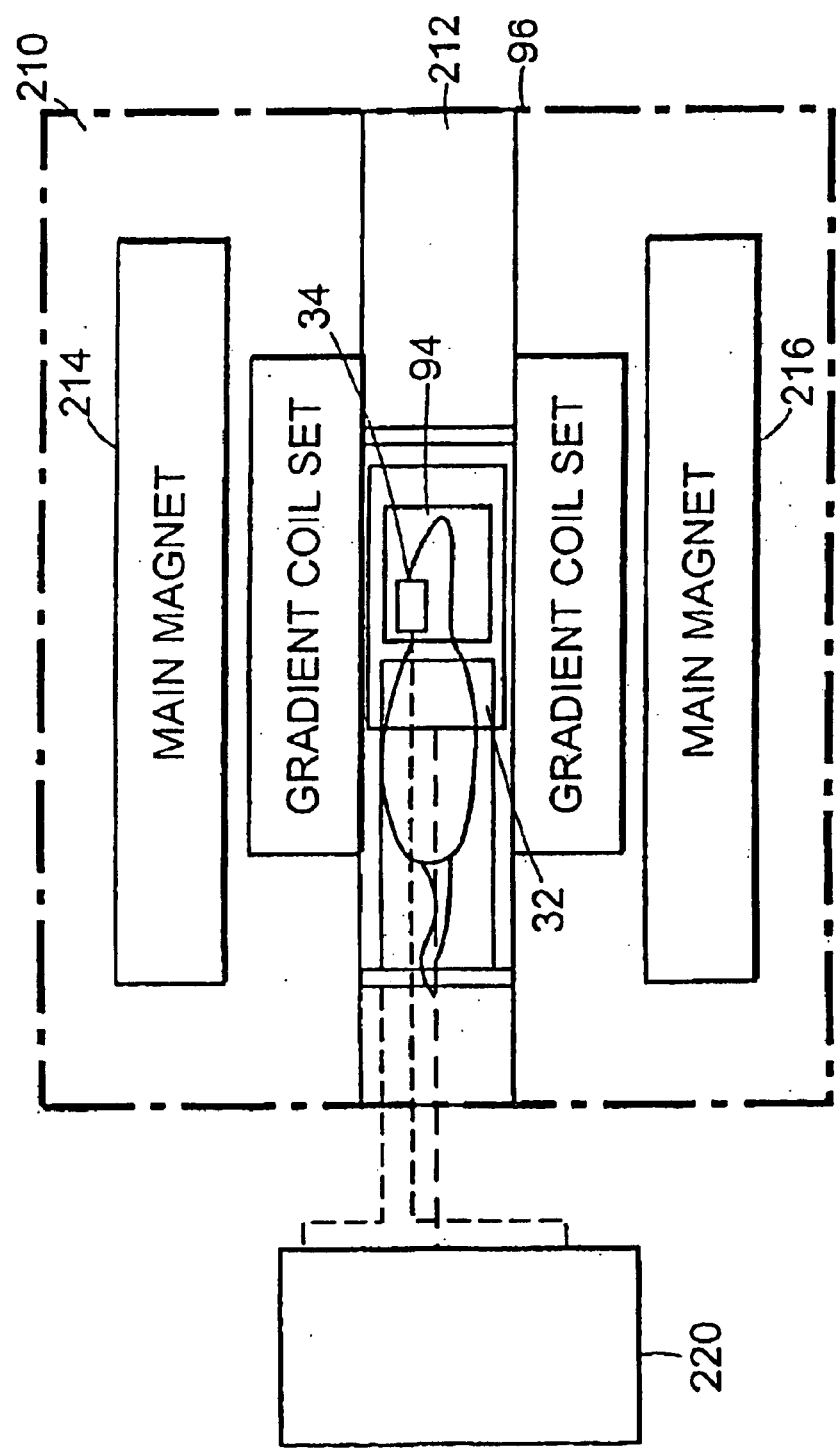
FIG. 8 is a schematic of the overall MRI system.

The bore 212, as shown in FIG. 8, is used in MR spectrometers used for functional imaging range from 10 cm to 100 cm. Human MR spectrometers range between 70–100 cm in diameter while a majority of the animal MR spectrometers used for functional imaging range from 10–50 cm. The front- and rear-end mounting plates can be made to fit any internal bore diameter in this range. Hence the multi-cylindrical dual coil animal restrainer can be used in both full body human spectrometers and dedicated smaller bore animal spectrometers.

The support rods 50 position the front-end and rear-end mounting plates 46 and 48 relative to each other and maintain the planes of the plates parallel to each other and perpendicular to the longitudinal axis 54. In addition, the support rods 50 are of such a size and material characteristics that the minor movement of the rear-end mounting plate 48 would not affect movement into the front-end mounting plate 46.

In one embodiment, the support rods 50 are connected to the mounting plates 46 and 48 by a damping mechanism such as rubber gaskets to further reduce transmission of movement caused on the rear-end mounting plate 48 to propagate to the front-end mounting plate 46.

The front-end mounting plate receives a docking post 64 which is part of the head retainer 40, as explained in further detail below. In an embodiment, the entire mounting unit is formed of a non-metallic transparent material such as Plexiglass™ or Nylon to minimize the influence on the magnetic fields.

Figure 3:
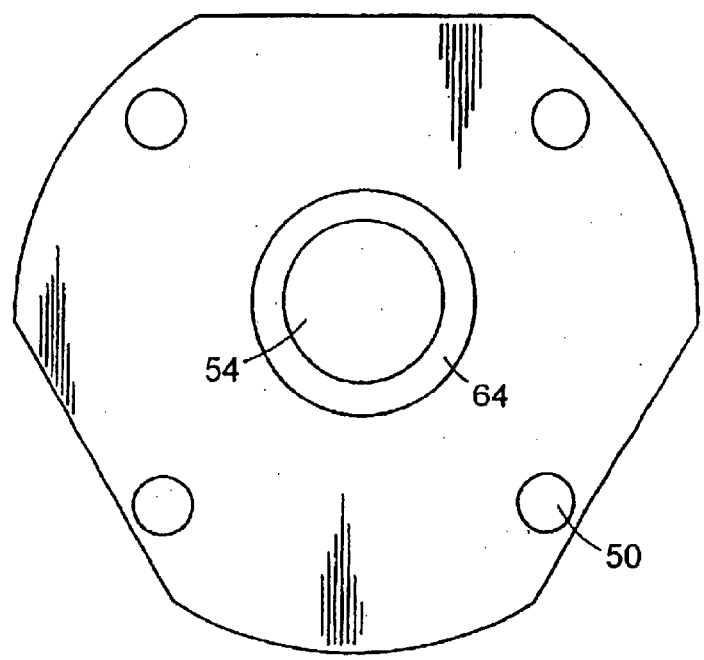
FIG. 3 is a front view of the front-end mounting plate.

Referring to FIG. 3, the front view of the front-end frame plate 46 is shown. The support rods 50 are extending through the mounting plate 46. In addition, in that the mounting plate 46 is transparent, the positioning tube 64 can be seen.

Figure 4:
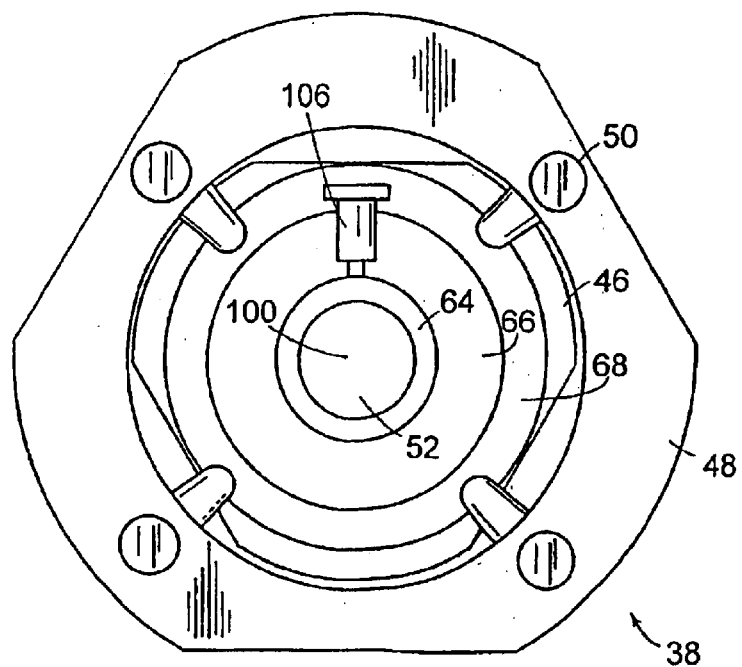
FIG. 4 is a rear perspective view of the chassis unit looking from the rear-end mounting plate.

Referring to FIG. 4, a rear perspective view of the mounting unit 38 is seen. The rear-end mounting plate 48 has the cylindrical opening 56 which is surrounded by the support rods 50 that extend parallel to and spaced from the longitudinal axis 54 of the frame. The support rods extend to the front-end mounting plate 46. The front-end mounting plate 46 has the hole 52 surrounded by a positioning tube 64. Encircling the positioning tube 64 is an annular groove 66 defined by the positioning tube 64 and an annular ring 68. In an embodiment, the annular groove 66 receives a resilient gasket 70 to improve dampening of motion as explained in further detail below.

Figure 6:
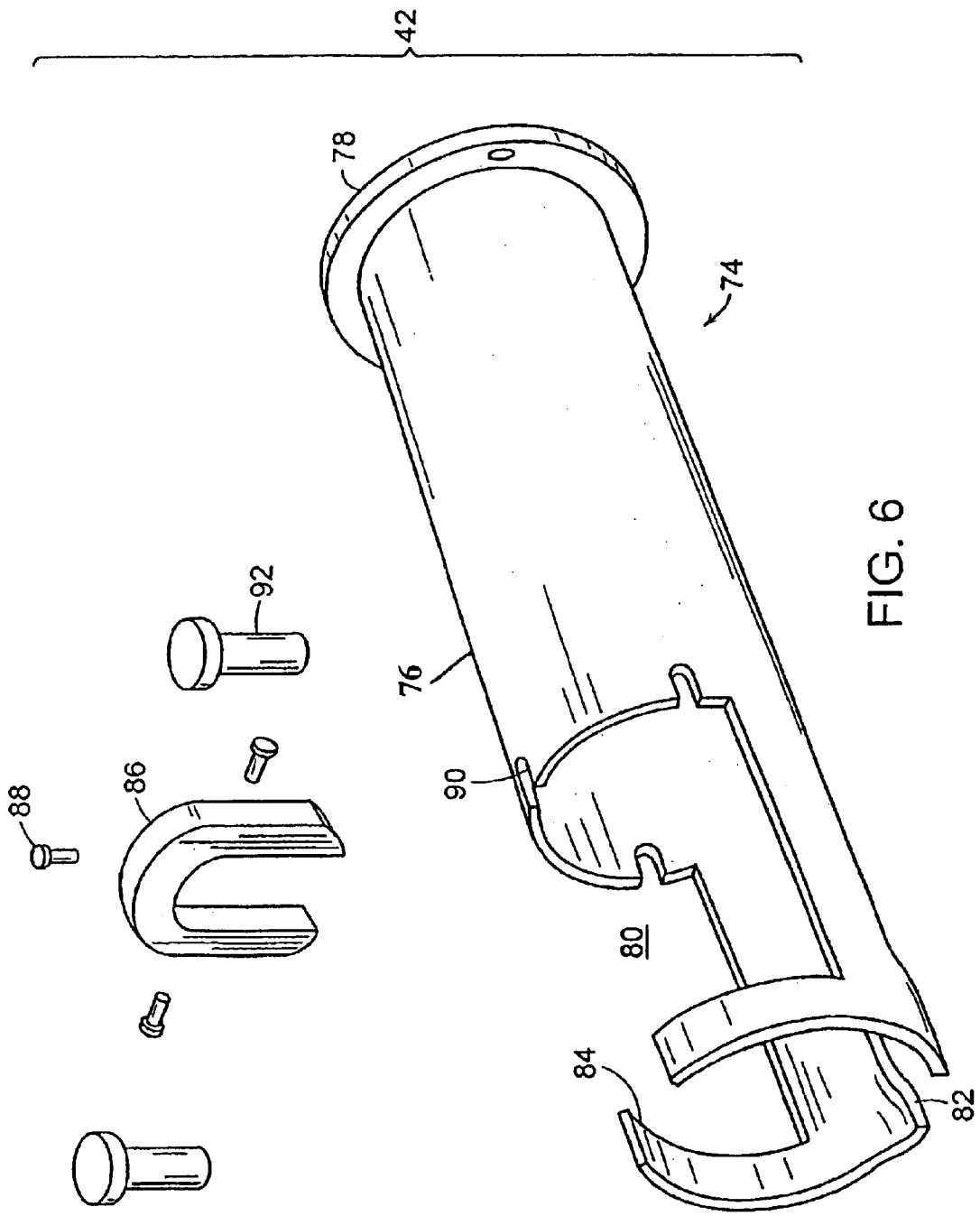
FIG. 6 is a side perspective view of the body tube and a shoulder bracket of the body restraining unit.

Referring to FIG. 5, the body retainer 42 has a body tube 74 which in a preferred embodiment, is Plexiglass™. The tube 74 has a cylindrical thin wall section 76 and a flange 78 for securing to the rear-end mounting plate 48. The thin wall section 76 has a cut-out portion 80, as seen in FIG. 6, which allows access to the head restraining unit 40. In addition, there is a slot 82 and an opening 84 into the cut-out portion 80 to prevent coupling of the body retainer 42 with the head retainer 40, as explained in further detail below.

Still referring to FIG. 6, the body retainer 42 also has a shoulder holder 86. The shoulder holder 86 is retained on the thin wall section 76 by a plurality of fasteners 88 received in slots 90 on the thin wall section 76.

The shoulder holder 86 limits movement of the shoulder of the animal toward the head retainer 40. In an alternative, the shoulder of an animal can be a pair of pins 92 as shown in phantom which drop into holes in the thin wall section 76 of the body tube. The choice of the shoulder holder 86 or the pins 92 is dependent on several factors including the size and type of animal to be restrained.

Figure 7A:
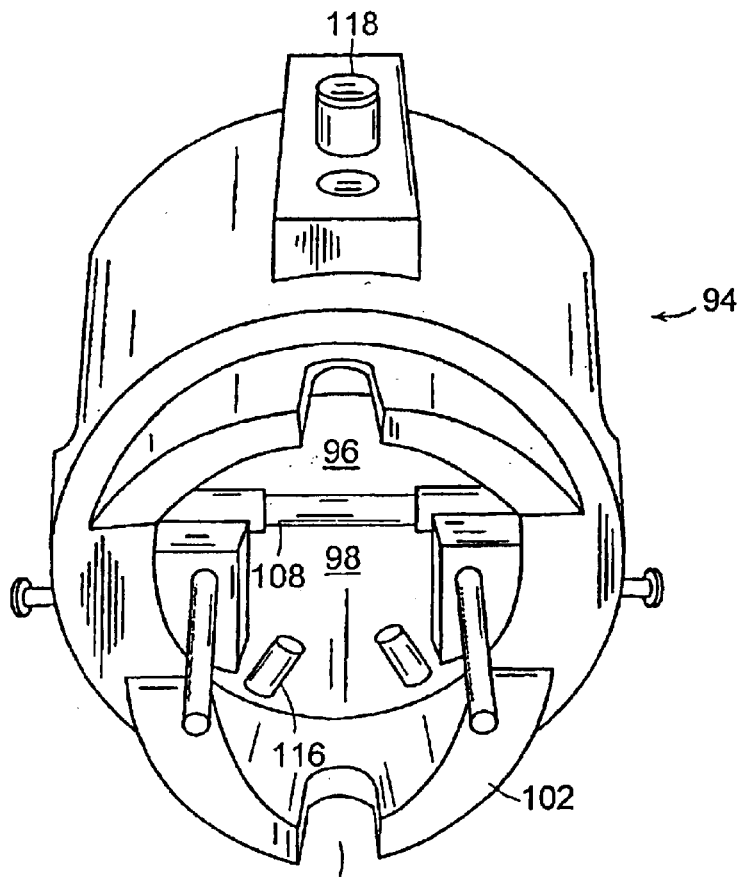
FIG. 7A is a front perspective view of the cylindrical head holder.

Referring to FIG. 7A, the head retainer 40 has a head holder 94 and the position tube 64, as seen in FIG. 2. The head holder 94 has a bore 96 which receives the head of the animal. The head is received from the other end of the head holder 94 from that shown in FIG. 7A. An aperture 98 extends from the bore 96 to communicate with an aperture 100 in the position tube 64 as seen in FIG. 4.

A pair of flanges 102 extend outward on the head holder 94 to encircle the position tube 64. Each of the flanges 102 have a slot 104 to accept a fastener 106, as seen in FIG. 4, to secure the head holder 94 to the position tube 64 of the head restrainer 40.

Figure 7B:
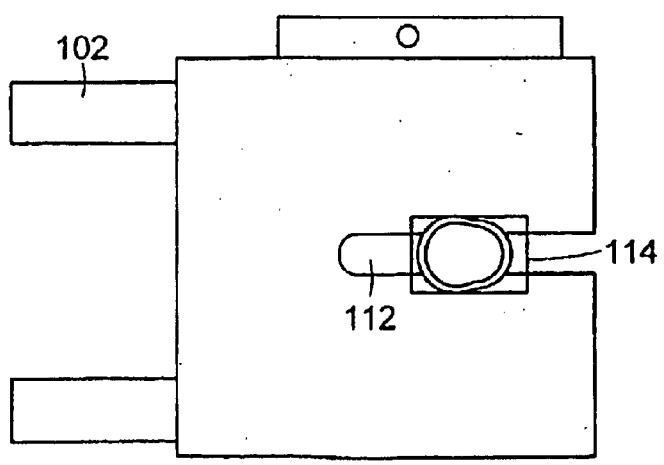
FIG. 7B is a side view of the head holder.
Figure 7C:
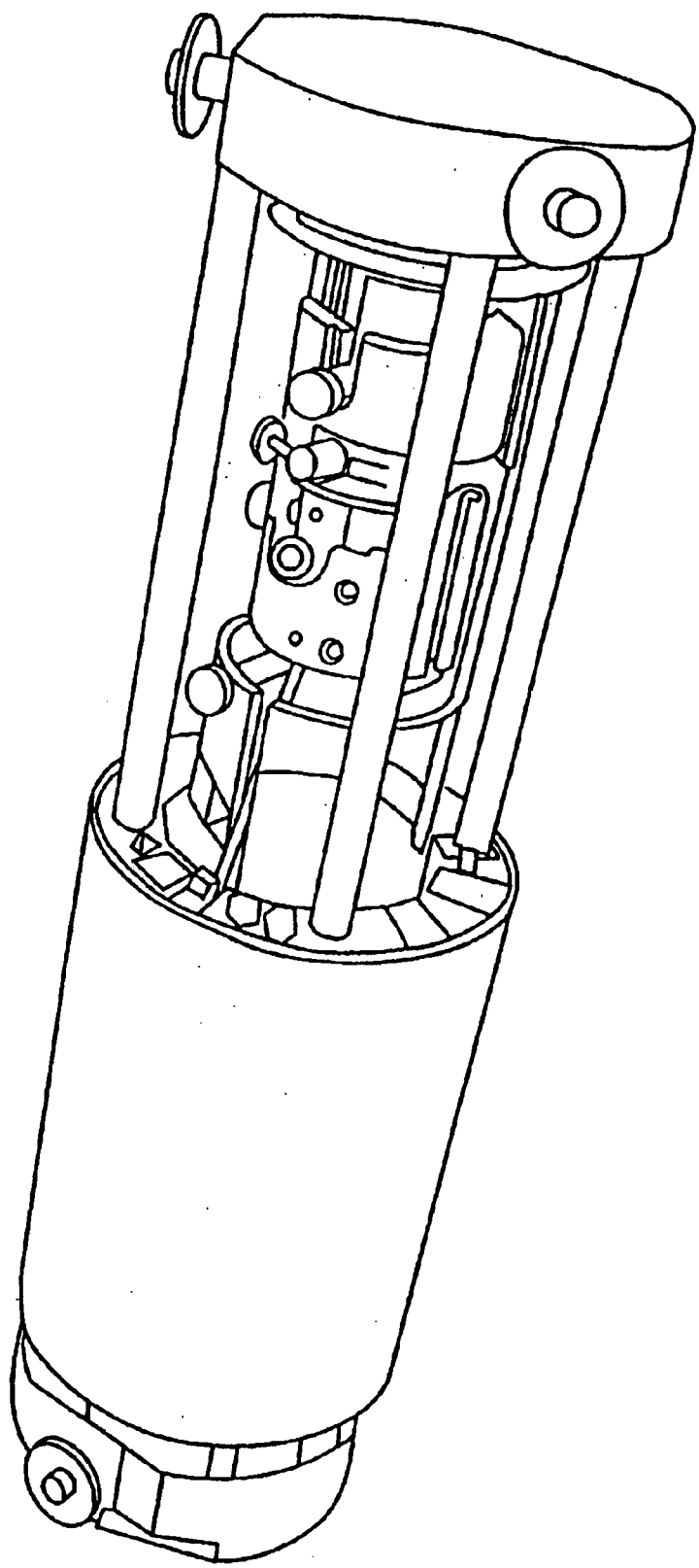
FIG. 7C is a perspective view of the assembled dual coil and restrainer system.

The head holder 94 has a bite bar 108 extending horizontally along a chord of he circular aperture 98 to provide a rest for the upper jaw of a restrained animal. Mounted through the top of the cylindrical head holder is a nose clamping screw 110 with a nose bar to secure the nose of a restrained animal to the bite bar 108. A pair of opposed lateral screw slots 112 are located in the sides of the cylindrical head holder 94 to receive lateral ear clamping screws 114, as seen in FIG. 7B.

The lateral ear clamping screw 114 has a washer shown in hidden line. The lateral ear clamping screws 114 are used to position the animal lateral in the head holder 94. In addition the head holder 94 has a pair of lower jaw screws 116 for restraining the lower jaw of the animal.

Figure 17A:
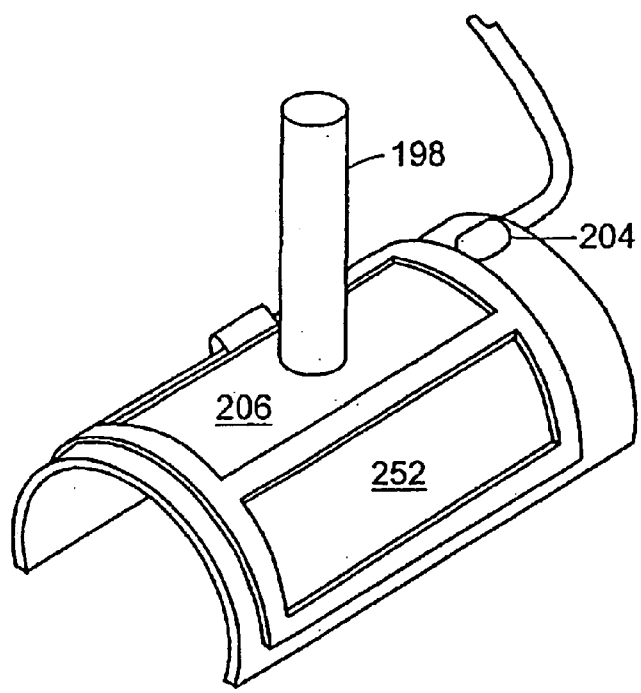
FIG. 17A is a view of a dome shape surface coil.

The head holder 94 also has a hole 118 for receiving a post 198 carried on the surface coil 34, as seen in FIG. 17A, to position the surface coil 34.

The surface coil 34, which is received in the bore 96 of the head holder 94 of the head restrained unit 40, works in conjunction with the volume coil 32 and a system operating controller 200 to produce the image. Referring to FIG. 8, a schematic of an embodiment of the invention is shown for using an MRI system to perform neuroimaging of animals. A conventional MRI device 210 for use with animals has a tunnel bore 212 in generally a range of 15 to 24 centimeters in diameter. A main magnet 214 and a gradient coil set 216 encircle the tunnel bore 212 as is known in the art.

The multi-cylindrical, dual-coil animal restrainer 30 including the restraining assembly 36 and the volume coil 32 and surface coil 34 are installed into the tunnel bore 212. The volume coil 32 is capable moving along the support rods 50 of the frame 38 as explained in further detail below. Both the surface coil 34 and the volume coil 32 are connected via wiring which extends out of the tunnel bore 212 to a transceiver unit 220 of the system operating controller 200 as explained in further detail with respect to FIG. 9. In one embodiment, the volume coil 32 transmits and the surface coil 34 is used for receiving. In other embodiments the surface coil both transmits and receives or the volume coil transmits and receives.

The image processing can be performed off-line on a 100 MHZ HP Apollo 735 workstation using IDL imaging software, Version 4.0 and analyzed on a Power Mac 60/66 using NIH imaging software, Version 1.56 (Apple Computer, Inc., Cupertino, Calif.). The stimulated and baseline images were subtracted to reveal regions of activation. The region of greatest activation was determined from the subtraction image. The corresponding region of the baseline and stimulated data sets were demarcated and the relative signal intensity was calculated on a pixel-by-pixel basis.

Referring to FIG. 9, a schematic of the interface between the RF coils 32 and 34 and a MRI transmit/receive system 218. Both the TEM volume coil 32 and the surface coil 34 is connected to a transceiver unit 220. The transceiver unit 220 has an RF transmitter 234, an RF receiver 226 and a system controller 228. The system controller 228 controls a pair of switching circuits 230 to transmit and receive the signal from the proper coil 32 or 34. In addition, the system controller 228 also can control an interface 230 to provide active tuning/detuning of the coils. For instance, if the TEM volume coil 32, also referred to as the body coil, is active, transmitting RF energy to the animal, the surface coil 34 is detuned in order to avoid interference. Conversely, when the surface coil 34 is receiving the MR signal from the animal, the TEM volume coil 32 is detuned.

Figure 10A:
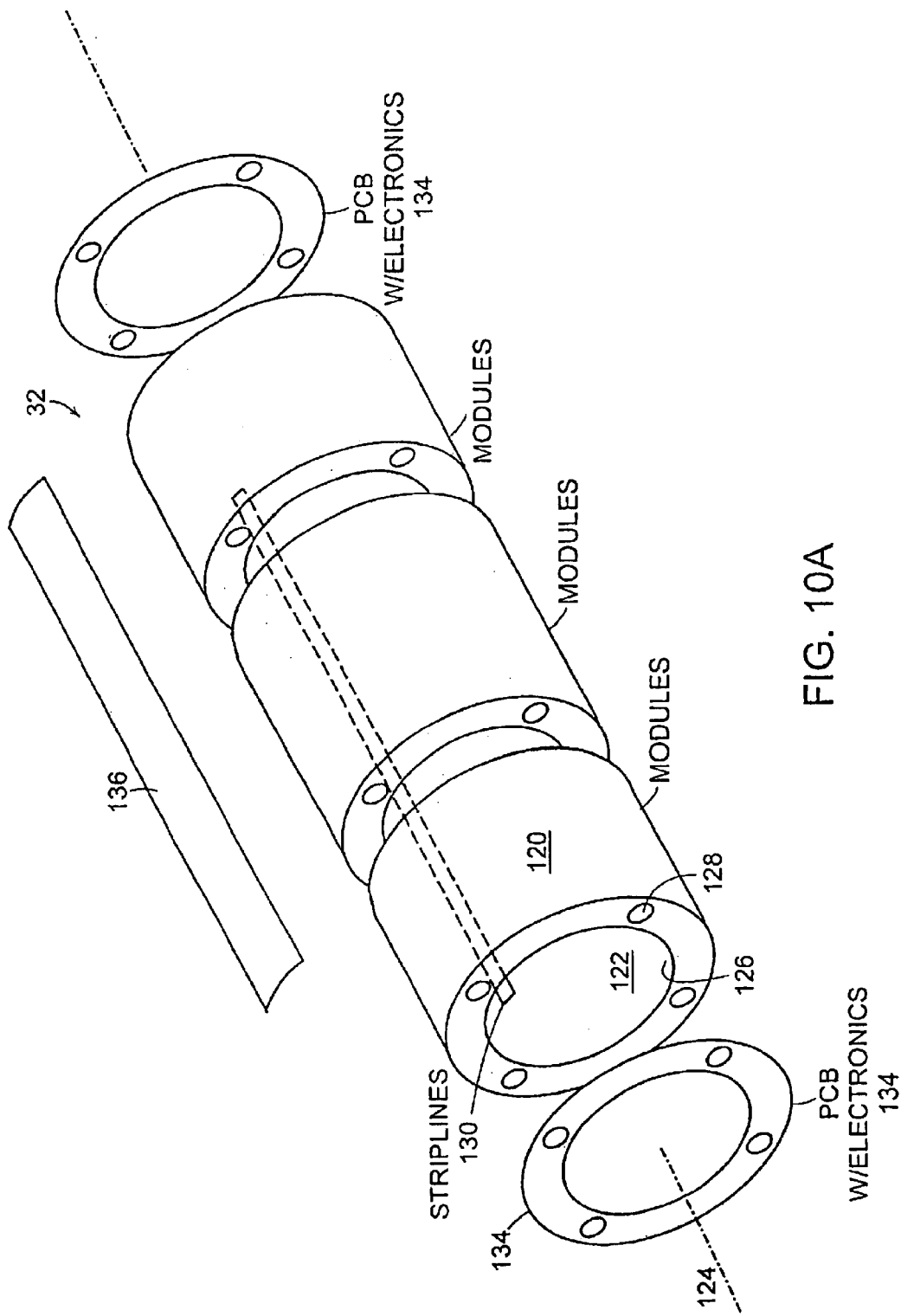
FIG. 10A is a exploded perspective view of a volume coil.

Referring to FIG. 10A, an exploded perspective view of the volume coil 32 is shown with the core shown in three segments. The volume coil 32 has a cylindrical non-metal core module 120. The core module 120 has a cylindrical bore 122 that extends through the core module 120 along a longitudinal axis 124. The cylindrical bore 122 defines an inner surface 126. In addition, the core module 120 has a plurality of bores 128 extending through the annular core module 120 parallel to and spaced from the longitudinal axis 124. The apertures 128 accept the support rods 50 to allow the volume coil 32 to move relative to the restraining assembly 36. The volume coil 32 has a plurality of conductive strip lines 130 extending parallel to the longitudinal axis 124 on the inner surface 126 of the core module 120.

Figure 10B:
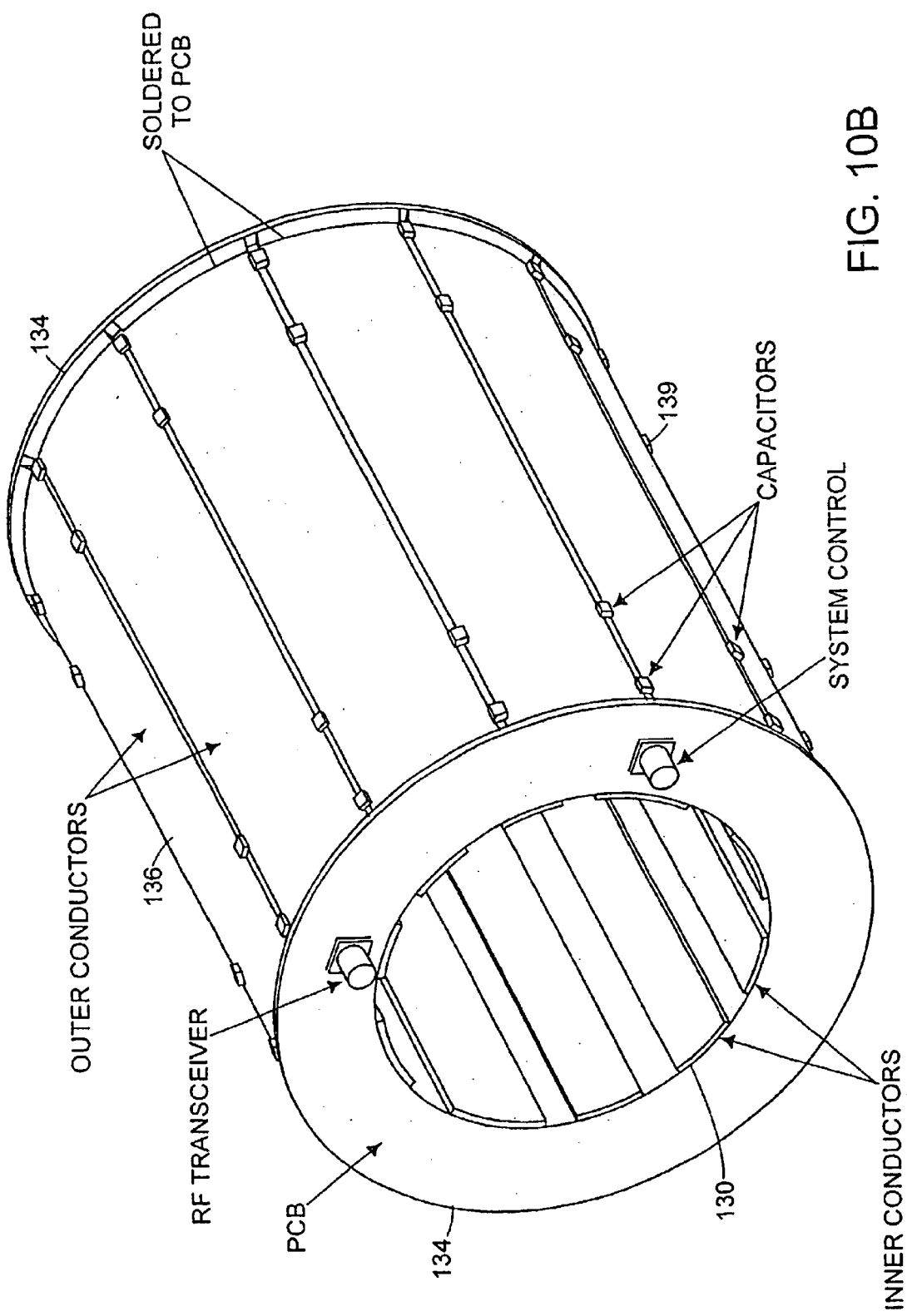
FIG. 10B illustrates the slotted volume coil.

The volume coil 32 has a pair of printed circuit boards (PCB) 134 mounted on the outer, side edges of the core module 120. In addition, the volume coil 32 has shielding 136 which overlies the core module 120 as seen in FIG. 10B. The shielding 136 is formed in strips to reduce the occurrence of eddy currents induced by the gradient coils 216, as seen in FIG. 8.

The shielding 136 in strips forms a plurality of coaxial slots 137 along the coil's length which serve to interrupt switched gradient induced eddy propagation. Reactively bridged azimuthal slots can extend around the TEM coil's outer wall, end walls, and inner "wall" further limit eddies, and extend the coil's frequency band and dimensional options.

In addition to the shielding 136 being strips, the conductive strip lines 130 creates slots 137 that interrupt eddy current propagation in the TEM coil divide the TEM cavity wall, front to back. The inner elements can be flat, copper foil double-sided strip-line elements, split coaxial elements, or single line copper conductors. FIGS. 10A and 10B shows copper foil strip line elements for strip lines 130. This segmented TEM coil combines the internal line element 130 with the external cavity segment, the shielding 136, forming a resonance circuit. Each functional element can be subdivided capacitively into one through four or more segments. Trimmer capacitors 139 on the outside wall of the FIG. 10B coil depict one such division. As in a simple surface coil, the number of capacitive divisions in each resonant unit can be chosen to be few when a more inductive, lower frequency performance of the TEM coil is desired. In contrast, each unit can be divided four or more times to affect the resonance frequency of this slotted TEM volume coil. Thereby electrically modified, the $B_1$ field generated by this subdivided coil will have improved field linearity and homogeneity.

Figure 11A:
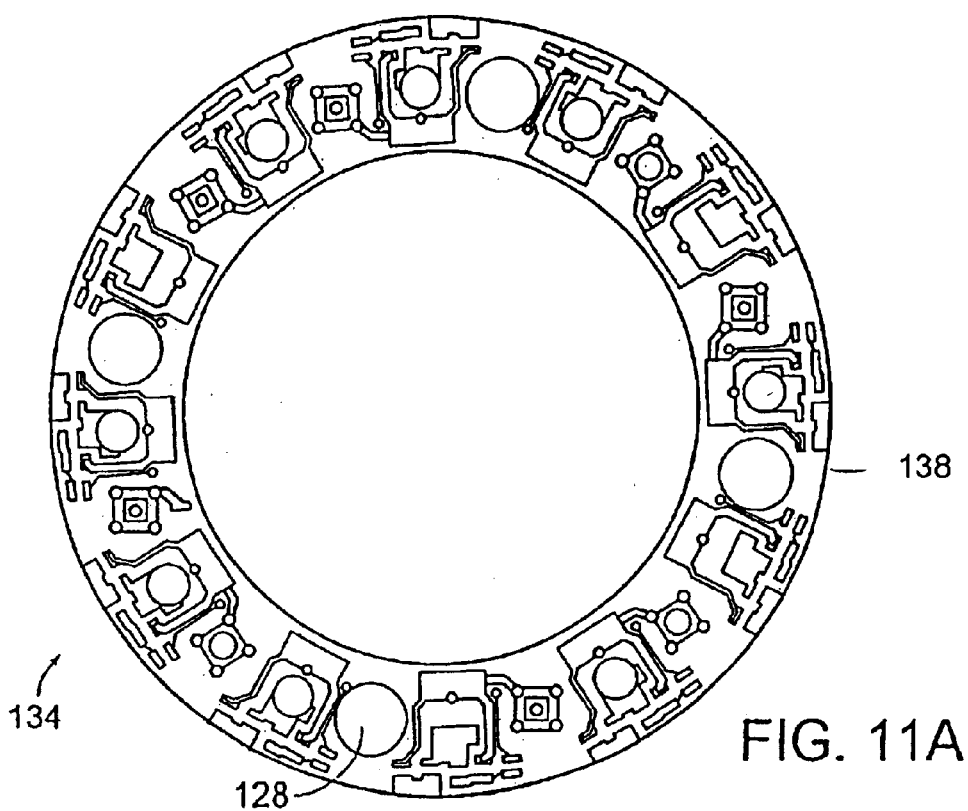
FIG. 11A is a view of the inner surface of a printed circuit board.
Figure 11B:
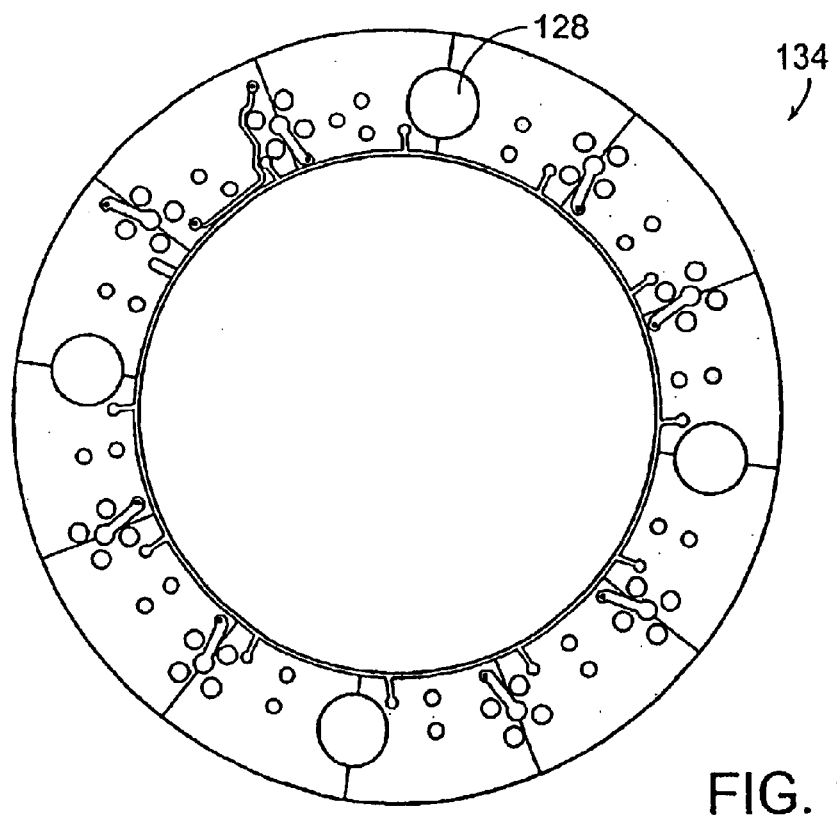
FIG. 11B is a view of the inner surface of a printed circuit board.

The printed circuit board 134 shown in FIG. 11A is an exposed surface 138, the surface of which faces away from the core module 120 of the volume coil 32. While FIG. 11B shows the inner surface, the surface which faces the core module 120. The inner surface which is covered with and is part of the shielding along with strips of shielding 136 shown in FIGS. 10A and 10B. The printed circuit board 134 has a plurality of components which are discussed with respect to FIGS. 12–15B.

Figure 12:
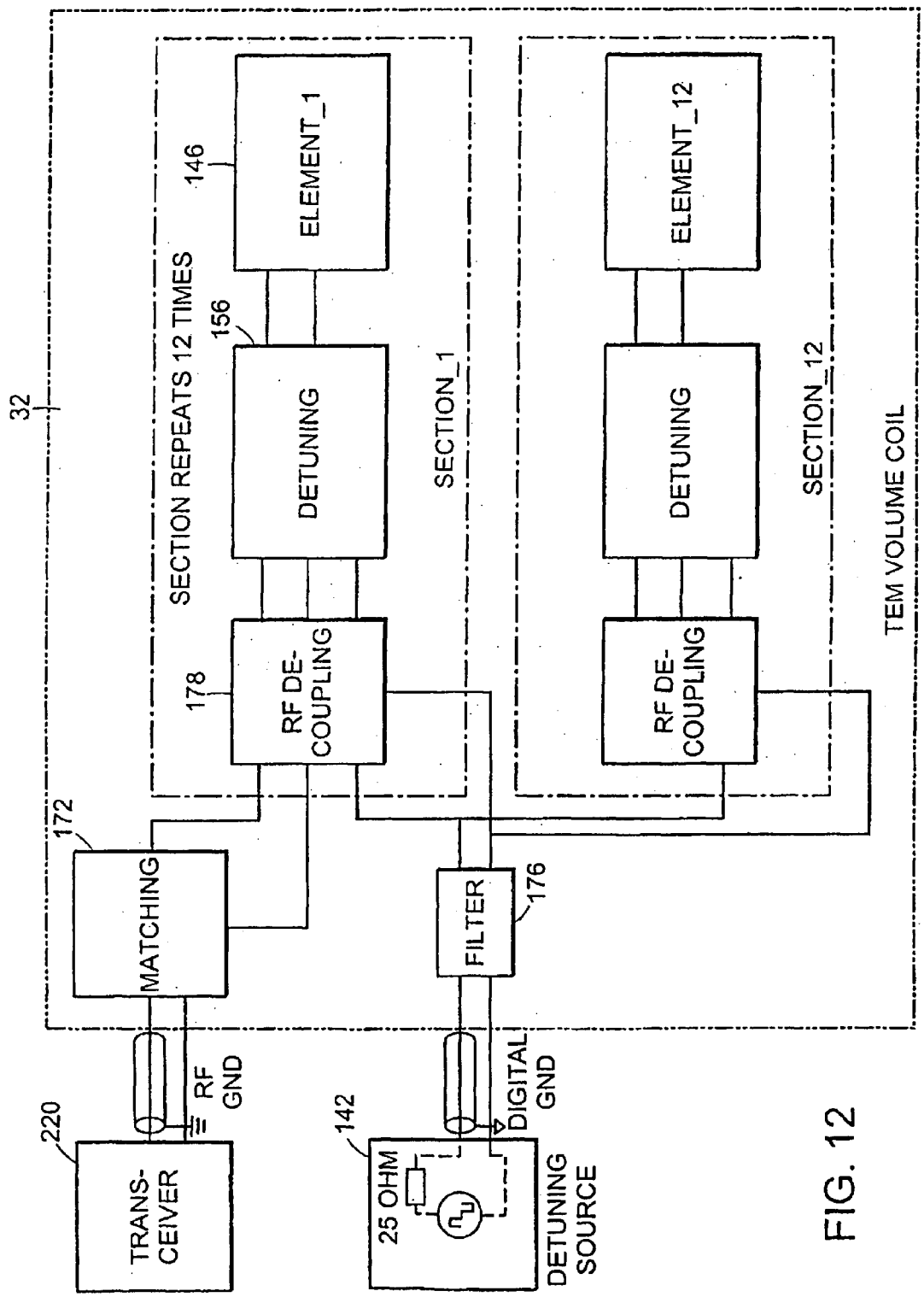
FIG. 12 is a schematic of circuitry associated with the volume coil.

A schematic of circuitry associated with the volume coil 32 is shown in FIG. 12. The volume coil 32 has a plurality of resonating elements 146 which include the strip lines 130 and the shielding 136. The elements 146 represented as number 1 and number 12 of a twelve element volume coil 32 are shown. It is recognized that the TEM volume coil 32 can have more or less elements 146, such as 8 or 16. The resonating elements 146 are connected to a detuning/tuning circuits 156 in order to move the resonance frequency of the resonating elements 146 away from the target resonance so as not to interfere with the receiving coil as explained in further detail below. The volume coil 32 in addition has a matching circuit 172 for adjusting the impedance of the resonating element 146 to that of the RF source. The TEM volume coil 32 is shown in FIG. 12 with the transceiver unit 220 and a detuning source 142 associated with its circuitry. The RF source 140, the transceiver unit 220 and the detuning source, 142, however, are not part of and are located remote from the volume coil 32 and are connected through coaxial cables which extend out of the cavity 212 and connect to the transceiver unit 220, as seen in FIG. 8. The volume coil 32 has an RF decoupling circuit 190. The RF decoupling circuit 128 ensures that the DC detuning signal does not interfere with the RF signal path.

Figure 13:
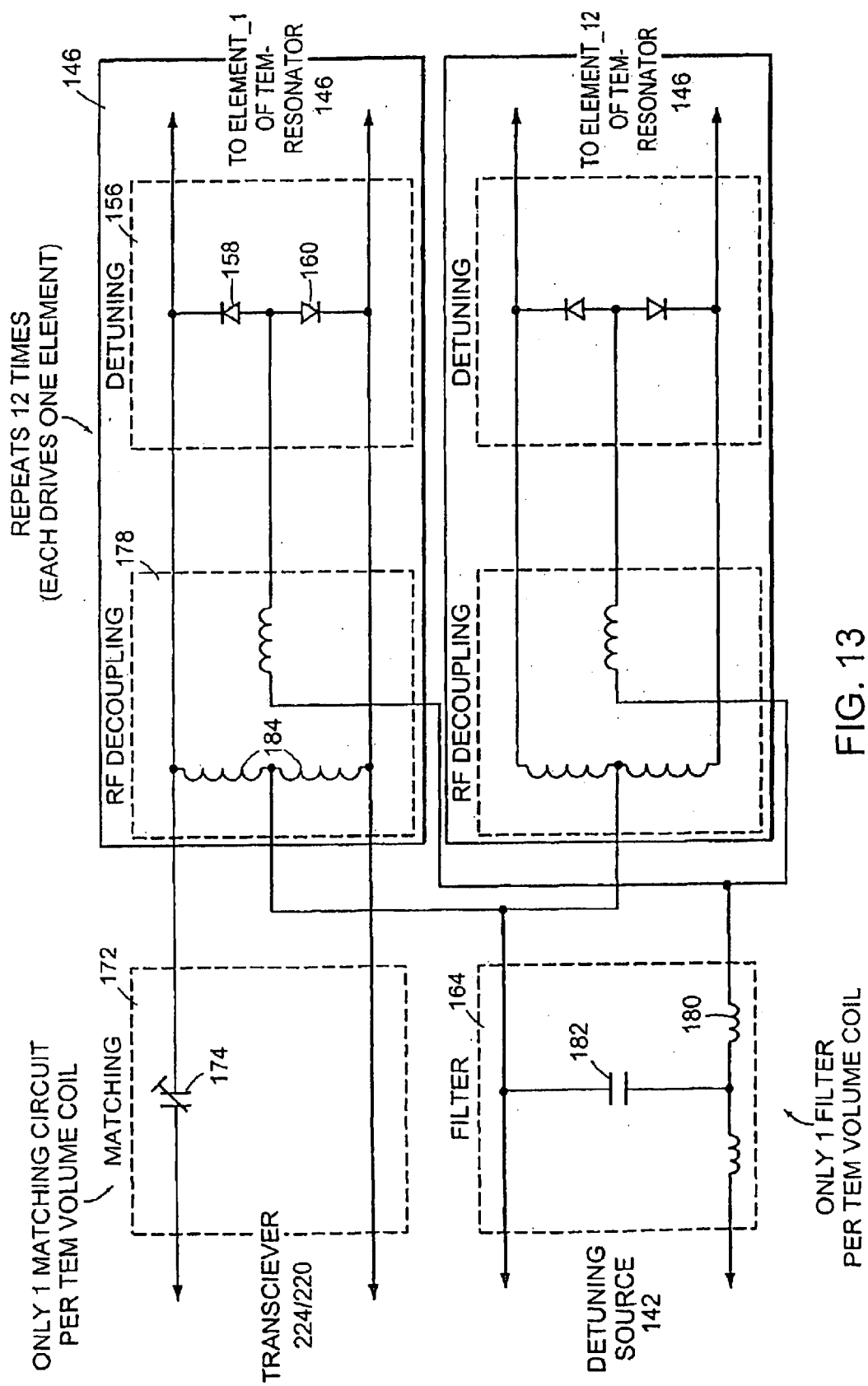
FIG. 13 is a schematic of circuitry system on the volume coil.

FIG. 13 shows a more detail view of circuitry associated with the volume coil 32 located on the volume coil 32. The matching circuit 172 includes a variable tunable capacitor 174. The detuning source 142 is connected to the detuning circuit 156 via a filter circuit 164 and the RF decoupling circuit 178. The filter circuit 164 has a pair of inductors 180 and a capacitor 182. The filter 164 is for separating the high frequency RF from interfering with the tuning/detuning signal. The RF decoupling circuit 178 has three radio-frequency chokes (RFC) 184 which represent low resistance to the DC current, but high impedance to the RF signal, thereby decoupling both signals from each other. From the detuning circuit 156 which contains a pair of pin diodes 158 and 160, the resonating element 146 is connected.

Figure 14:
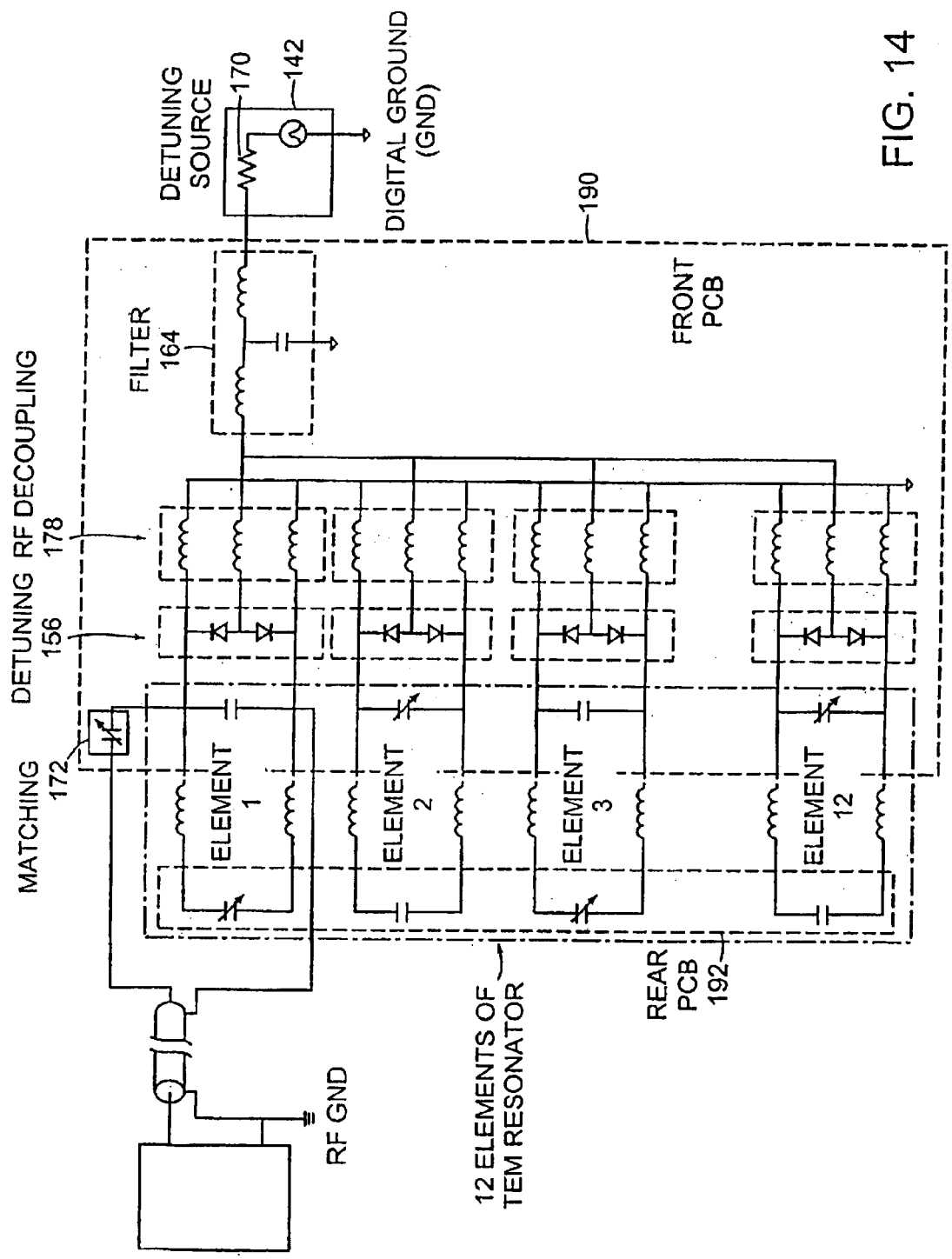
FIG. 14 is a schematic representation of circuitry associated of the volume coil.

FIG. 14 shows additional elements of the circuitry of volume coil 32. As indicated above, the volume coil 32 has several inputs including the RF source 140 from the RF transmitter 224 of the transceiver unit 220, the DC source 142 and a ground 144. The strip lines 130 are each part of a resonating element 146. The strip lines 130 are represented in the circuit as distributed inductor 148 in the resonating element 146. The strip lines 130, as represented by the inductors 148, are connected in series to a pair of capacitors 150 and 152. One of the capacitors is the variable, tuneable capacitor 152. In the embodiment shown in FIG. 14, the variable, tuneable capacitors 152 of one of the resonating element 146 is located on the front PCB 134 and the variable, tuneable capacitors 152 of the adjacent resonating elements 146 are located on the rear PCB 134; in that there are an even number of resonating elements 146, the variable, tuneable capacitors 152 are equally located on the front PCB and the rear PCB. The other capacitor, the capacitor 150, for each resonating element 146 is located on the other PCB 134 than that of the variable, tuneable capacitor 152.

In an alternative embodiment, all the variable, tuneable capacitors 152 of the resonating elements 146 are located on the front PCB 134. The other capacitor, the capacitor 150 is located on the rear PCB 134.

The front PCB 134 is represented by boxes 190 in FIG. 14 and the rear PCB 134 is represented by boxes 192. The stripes of shielding 136 are represented by a distributed inductor. The variable, tuneable capacitors 152 can be tuned manually or electronically. The capacitors 150 and 152 are each carried on the printed circuit board 134. One of the sets of the capacitors 150 and 152 and a strip line 130 in conjunction with the outer strip shielding 136 form an element which is connected to the detuning circuit 156.

Each of the detuning circuits 156 has a pair of diodes 158 and 160. In one embodiment, the diodes 158 and 160 are pin diodes. The RF decoupling circuit 178 has a plurality of inductors 162 (184). One of the detuning circuits 156 and one of the decoupling circuits 178 are each interposed between one of the resonating elements 146 and the filter circuit 164.

The filter 164 is connected to the DC source 142 through a resistor 170. The DC source 142 is used in operating the circuit in conjunction with surface coil 34 as explained below.

Still referring to FIG. 14, the RF source 140 and the matching circuit 172 are connected to one of the resonating element 146. The matching circuit 172 includes the variable tuneable capacitor 174 which is tuned manually.

Figure 15A:
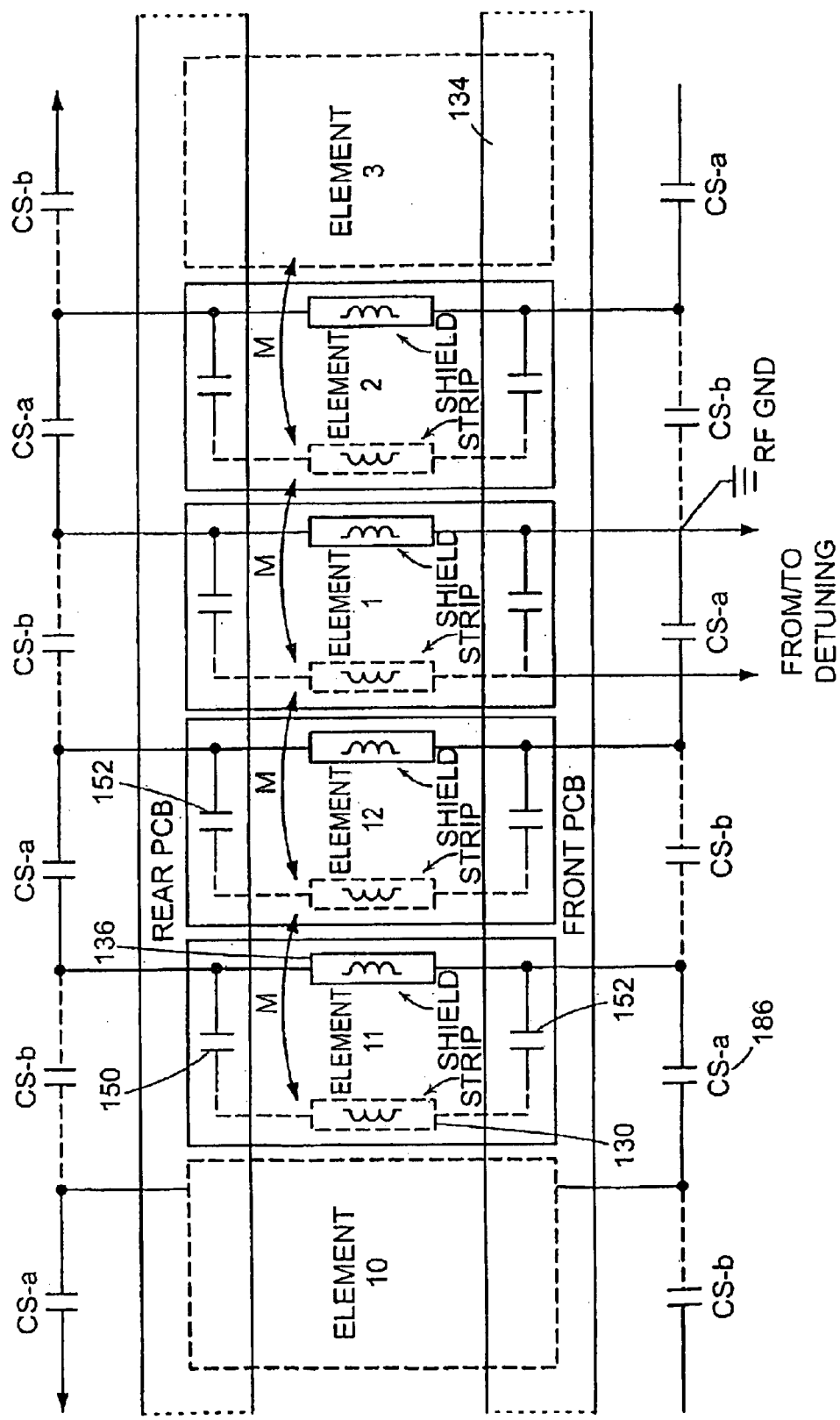
FIG. 15A is a schematic of the conductor circuitry of the volume coil.

Referring to FIG. 15A, a portion of the volume coil 32 is represented. In the embodiment represented in FIG. 15A, twelve elements are located on the volume coil 32. The strip lines 130 are represented by distributed inductors. Connected to the strip line 130 is a pair of capacitors in the series 150 and 152 wherein one of the capacitors 152 is a variable tuneable capacitor. In the embodiment shown in FIG. 1SA, the variable, tunable capacitors 152 is shown alternating from being on the front printed circuit board 134 to being on the rear printed circuit board 134 for every other resonating element. In addition, each element shows the shielding 136 which is the return path for the respected strip line 130. The adjacent strip lines 130 are mutually coupled.

As indicated above, the volume coil 32 has shielding 136 located on the outer surface of the core module 120. The strips of shielding 136 are connected to each other by capacitors located at alternative ends of the strips of shielding 136. The capacitors 186 are located on the outer surface of the resonating element as part of the shielding 136. Additional capacitors may be located at the other end of the strips of shielding 136 or alternatively they may be shorted in an effort to reduce the occurrence of eddy currents due to the activation of the gradient coils. The first element shown connected to a detuning circuit.

Figure 15B:
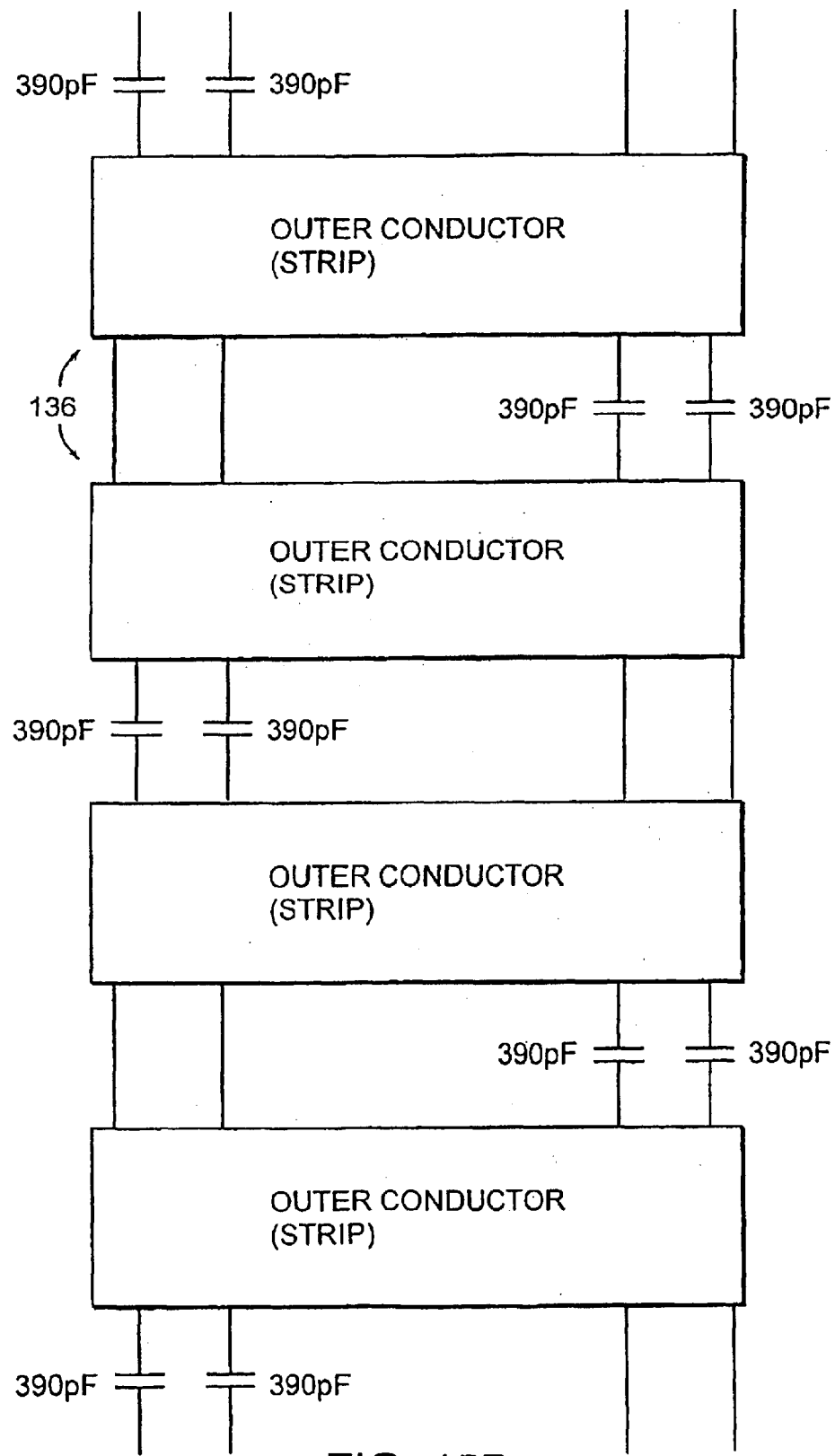
FIG. 15B is a schematic of interrelation of several of the strip of shielding.

A schematic showing the connection of adjacent strips of shielding 136 for a portion of the volume coil 32 is seen in FIG. 15B. The strips of shielding 136 are connected to each other by capacitors located on the outer surface of the resonating element as part of the shielding such as seen in FIG. 10B. The capacitors are located at alternative ends of the strips of shielding 136. In the embodiment shown, the other end of the strips of shielding 136 are shorted to reduce the occurrence of eddy currents as discussed above.

Working with the volume coil 32 is the surface coil 34 that can be used in one mode to receive the MR signal from the animal. In another mode, the surface coil 34 both transmits and receives the RF.

The surface coil 32 can take various shapes. The surface coil 32 can have a single loop as described with respect to FIGS. 16A–16B or have multiple loops arranged in a dome shaped surface coil 196 as seen in FIGS. 17A and 17B.

Figure 16A:
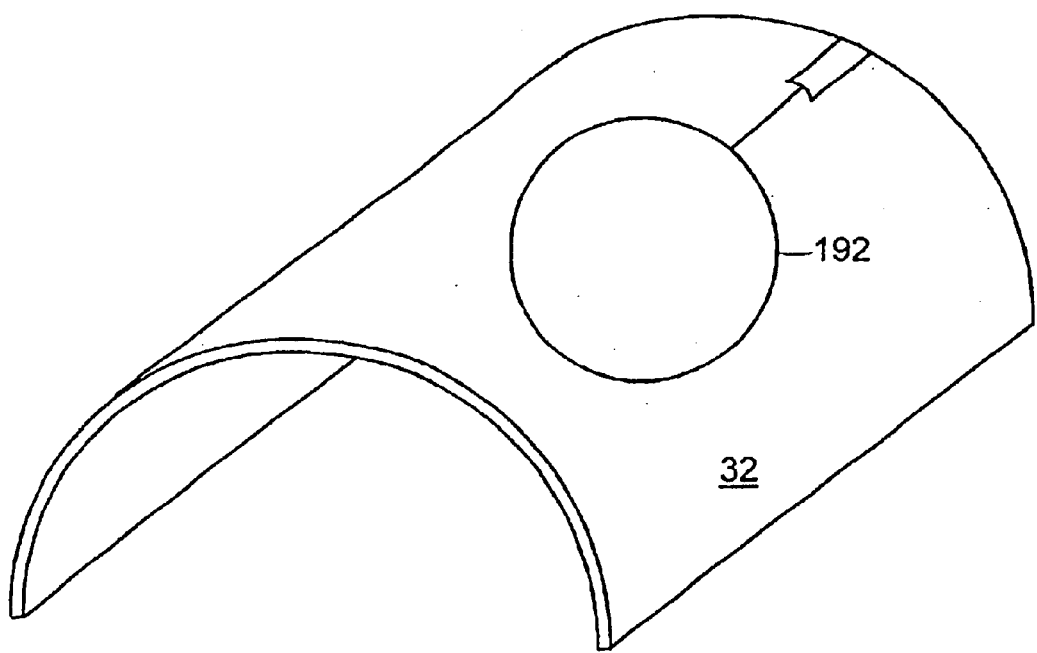
FIG. 16A is a view of a single loop surface coil.
Figure 16B:
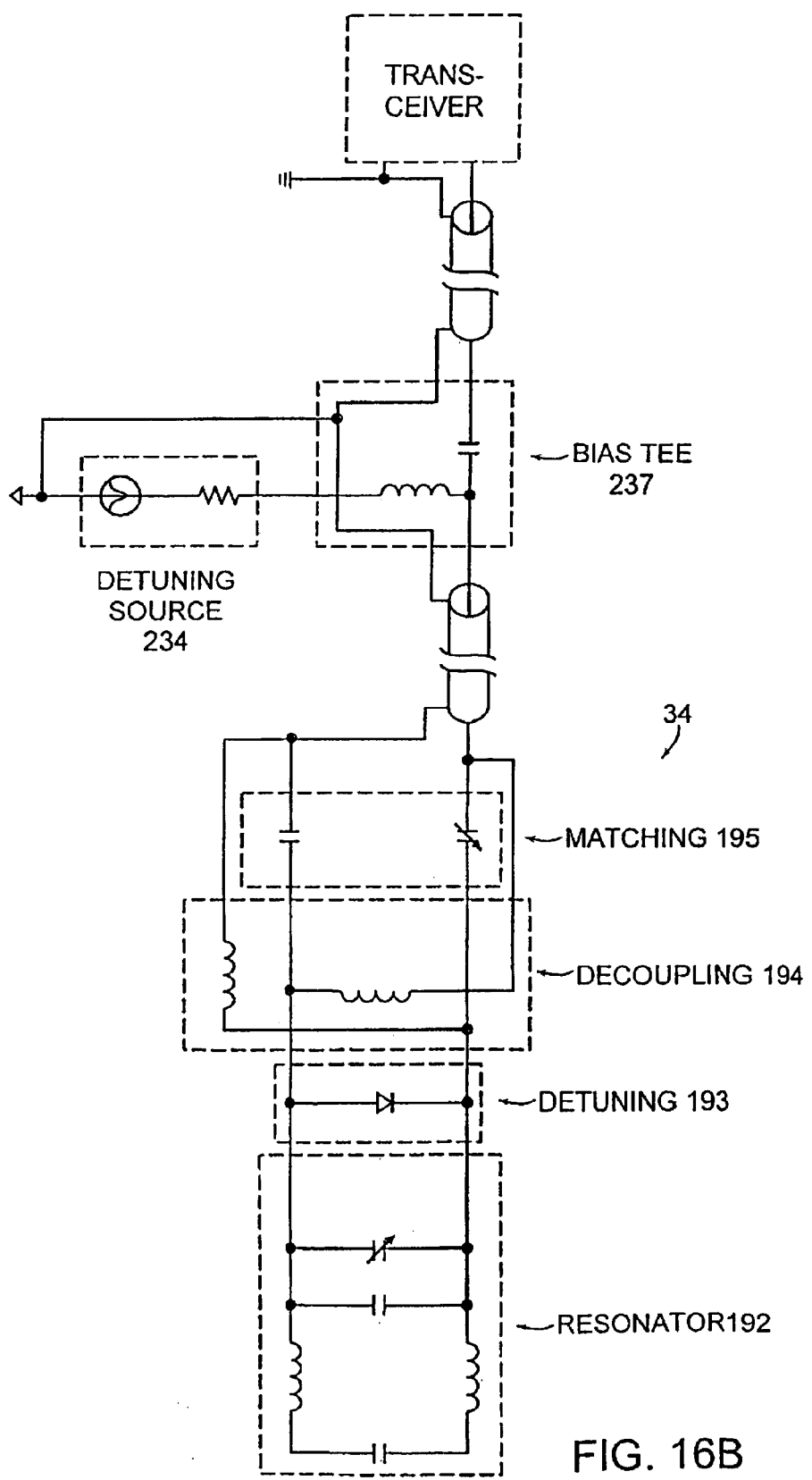
FIG. 16B is a is a schematic circuit of a single loop surface coil.
Figure 17B:
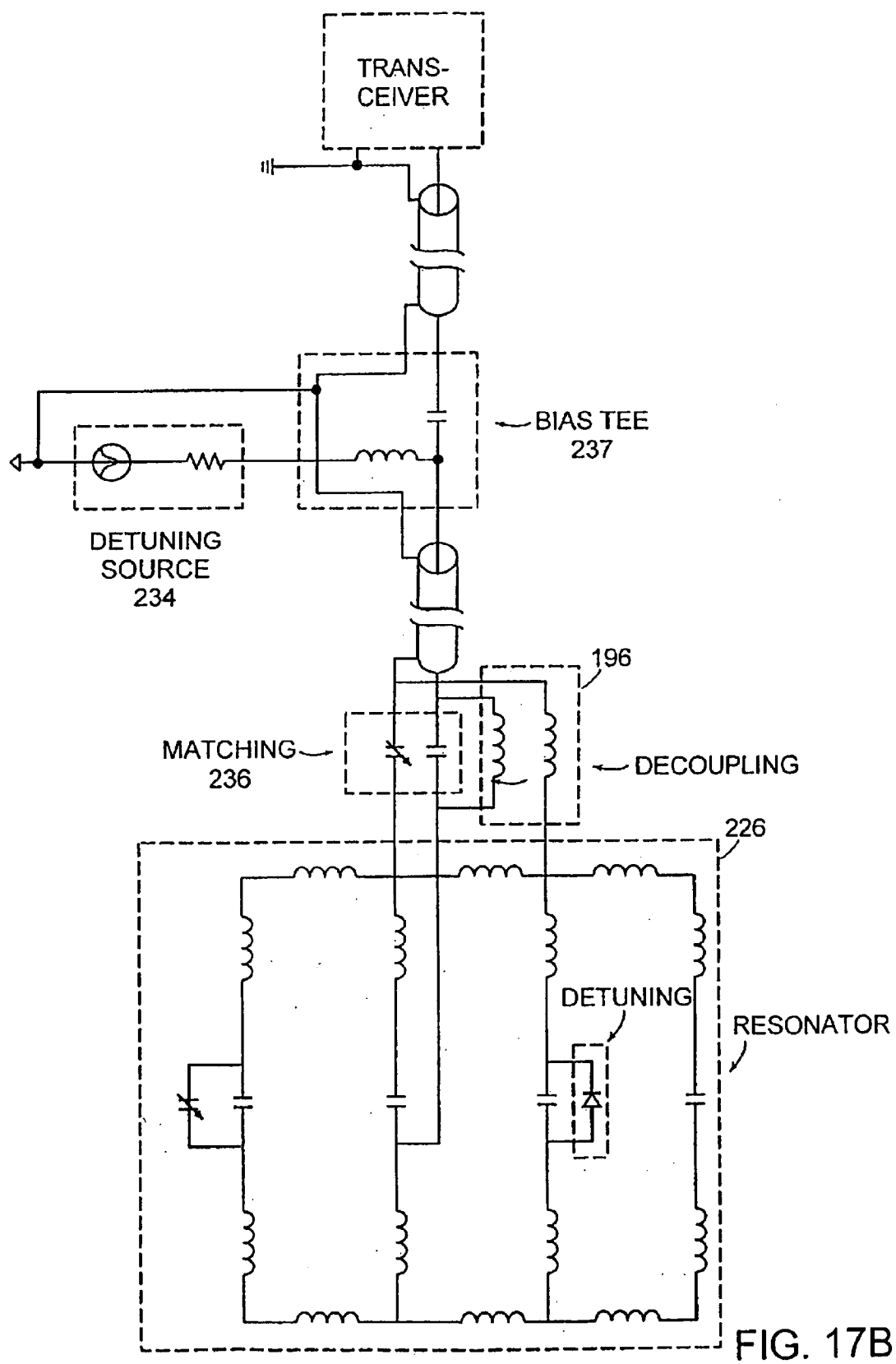
FIG. 17B is a schematic of circuitry of a dome surface coil.

Referring to FIGS. 16A and 16B, a surface coil 32 with a single loop is shown. The circuitry of the surface coil of FIG. 16A is shown in FIG. 16B. The resonating element 192 of the single loop has a pair of metallic strips with interposed capacitors schematically shown in FIG. 16B. The single loop surface coil has a detuning circuit 193 and a decoupling circuit 194.

The single loop surface coil 34 has a connection to the transceiver and the detuning source. The single loop surface coil 34 has a post 198 for attaching to the head holder 94 or other device as explained below.

An alternative to the single loop surface coil 34 of FIGS. 16A and 16B is a multiple loop dome shaped surface coil device 252 shown in FIG. 17A. FIG. 17B is a schematic of the multiple loop surface coil 196 of the dome shaped device 252.

The surface coil 196 has a post 198 as seen in FIG. 17A for attaching to the head holder 94 or other device as explained below. The surface coil 196 a pair of connectors 204 and 206 which are connected to the RF source 140 and the DC source 142. Similar to the volume coil 32, the surface coil 196 has a detuning circuit 234 and matching capacitor circuit 236. Also similar to volume coil 32, the surface coil 196 has the inputs of the RS source 140, the DC source 142 and the ground 144.

The surface coil 196 has a plurality of resonating elements 226 each with a strip line which is represented by an inductor. Both fixed and tuneable capacitors are deployed. The tuneable capacitor is used to adjust the resonance frequency with a capacitor is used to match the circuit.

With the multi-cylindrical, dual-coil animal restrainer 30 including the volume coil 32 and the surface coil 34 described, a method of performing neuroimaging is described.

Figure 18:
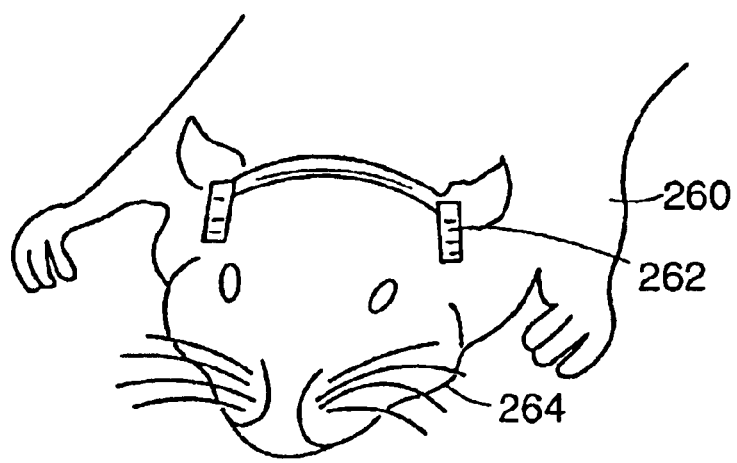
FIG. 18 is a front perspective view of a rat with the semi-circular ear piece.
Figure 19:
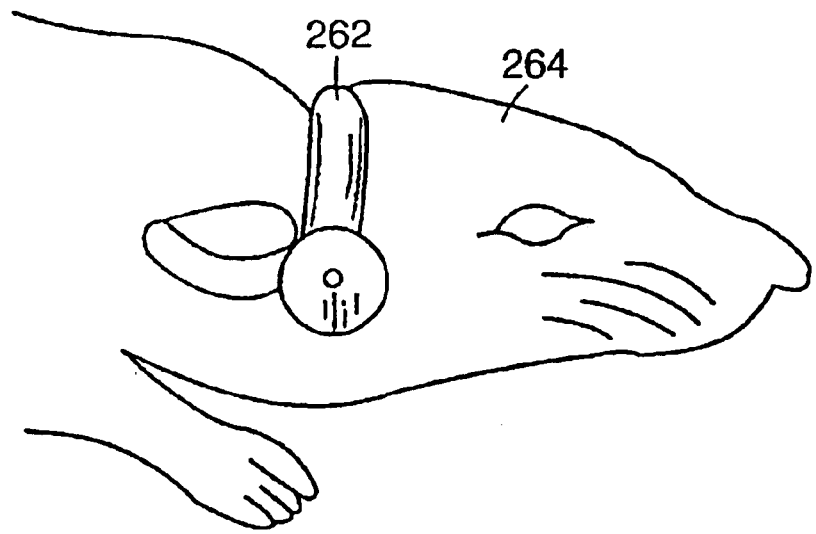
FIG. 19 is a side view of a rat with the semi-circular ear piece.

The animal 260 is lightly anesthetized prior to insertion into the restraining system 30. As shown in FIGS. 18 and 19, a semi-circular ear piece 262 is fitted over the head 264 of the animal 260 whereupon the animal's head 264 is placed into head holder 94.

Figure 21:
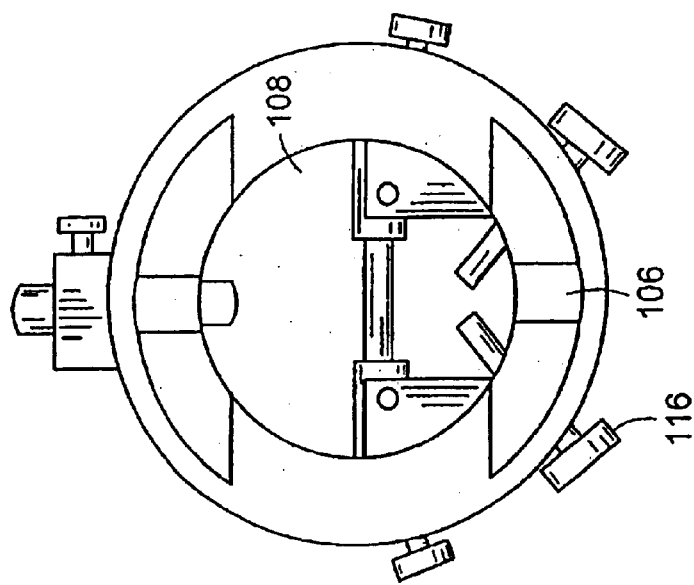
FIG. 21 is a front view of a rat in the cylindrical head holder.
Figure 20:
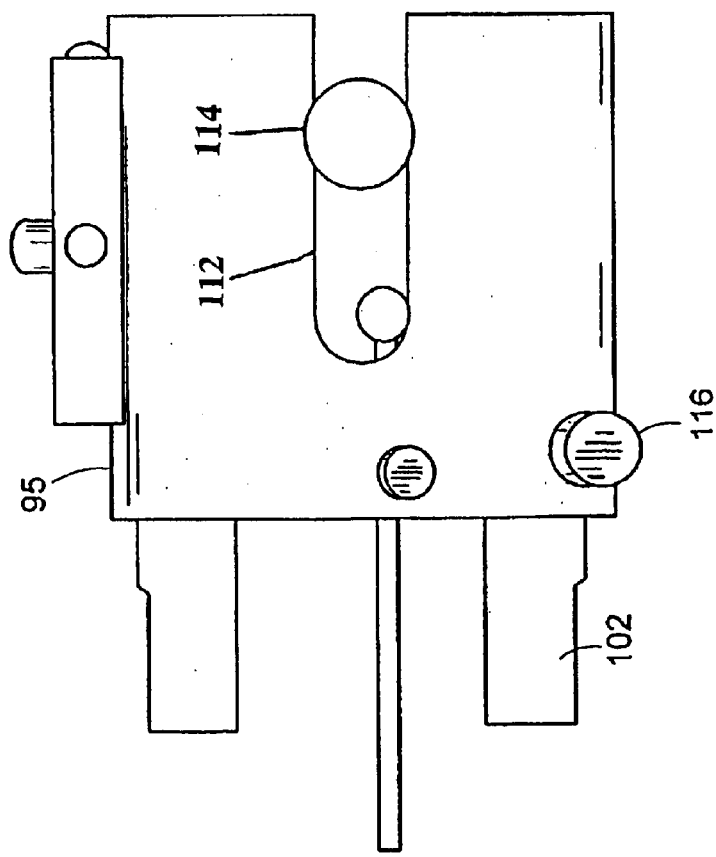
FIG. 20 is a side view of a rat in the cylindrical head holder.

Referring to FIGS. 20 and 21, lateral ear clamping screws 114 are inserted through the pair of lateral screw slots 112 and tightened against divots in a semi-circular ear piece 262 to prevent the animal 260 from moving horizontally. The upper jaw of the animal 260, such as a monkey, is fitted over the bite bar 108 and nose clamping screw 110 is tightened against the snout of the animal to secure it to the bite bar 108 and thereby eliminate vertical movement maintaining a stereotaxic position of the animal's head.

FIG. 22 shows a restraining jacket 268 used to restrain the animal 260. The jacket 268 is made of a looped lined, such as marketed under the name Velcro™, non-flexible fabric with a hooked closure 270, such as marketed under the name Velcro™. The restraining jacket 268 has a pair of arm holders 272 and a pair of leg holders 274 for further restrict the animal's movement. The jacket 268 has holes for the animal's head and rear/tail 276 and 278, respectively.

Figure 23:
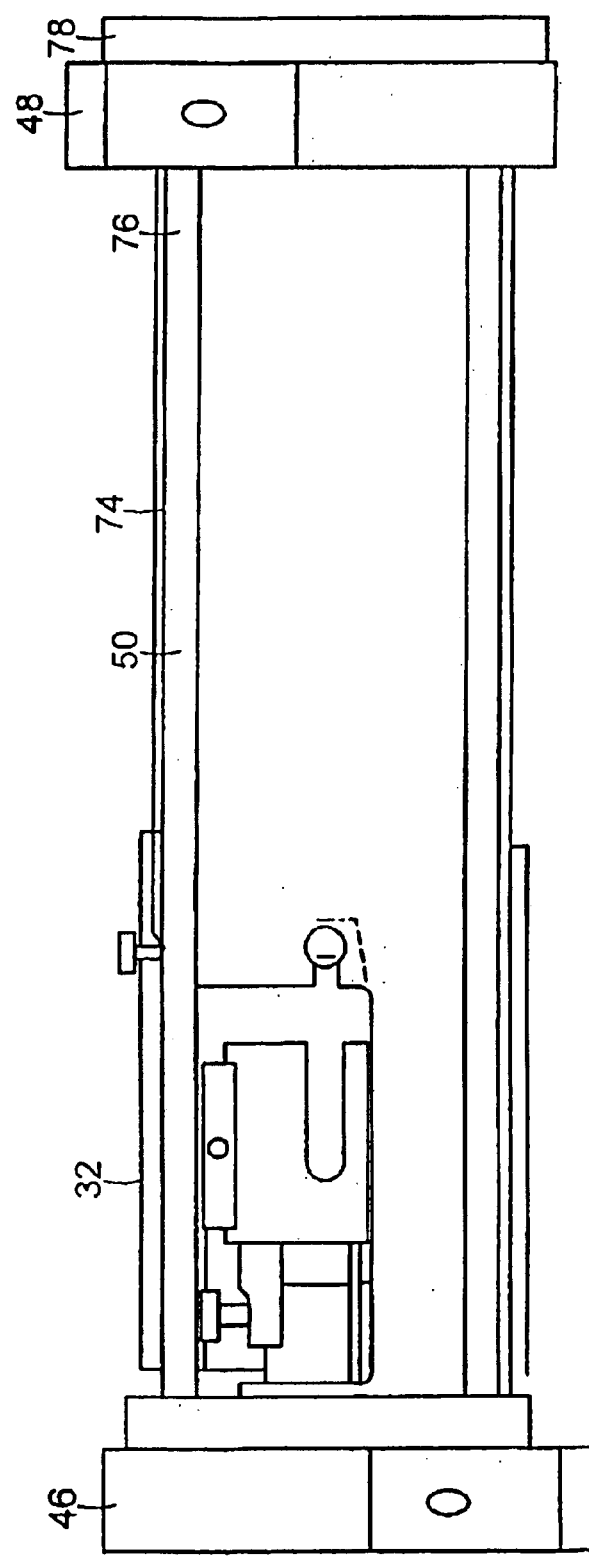
FIG. 23 is a side view of a rat in the assembled fMRI restraint.

Referring to FIG. 23, with the head of the animal 260 retained in the head holder 94, as shown in FIG. 20 and 21, and the body of the animal in the retraining jacket 268, the head holder 94 is fixedly mounted to the position tube 64 by a pair of fasteners 106. The pair of flanges or lips 102 extend outward on the head holder 94 to encircle the position tube 64. Each of the flanges 102 have a slot 104 to accept the fastener 106. The position tube 64 is received with a gasket 70 interposed.

With the head retraining unit 40 attached to the mounting unit 38, the body tube 74 of the body restraining unit 42 is slipped through the cylindrical opening 56 of the rear-end mounting plate 48 and receives the body of the animal 260 in the restraining jacket 268. The shoulder holder 86 or pins 92 are installed limits movement of the shoulder of the animal toward the head restraining unit 40.

The surface coil 34 is installed into the head restraint 40 prior to the installation of the head 264 of the animal 260 and lowered into position after the animal is in position in the body tube 74 and the head restraining unit 40. The volume coil 32 is slid along the support rods 50 to the proper position encircling the animal 260.

The multi-cylindrical, dual-coil animal restrainer 30 is installed into the tunnel bore 212 of the MRI device 210. Before testing the anesthesia has worn off so that the animal is conscious. The MRI transmit/receive system 242 controlling the surface coil 34 and the volume coil 32.

Figure 24D:
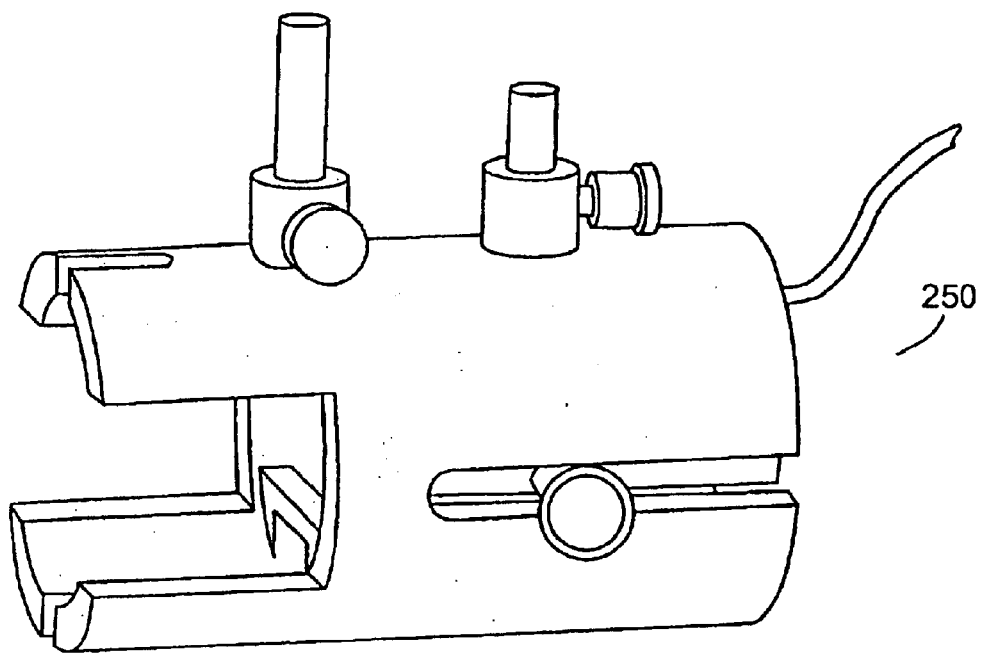
FIGS. 24A–24D illustrate head restrainer, support frame and surface coil components of a preferred embodiment of the inventions.
Figure 24A:
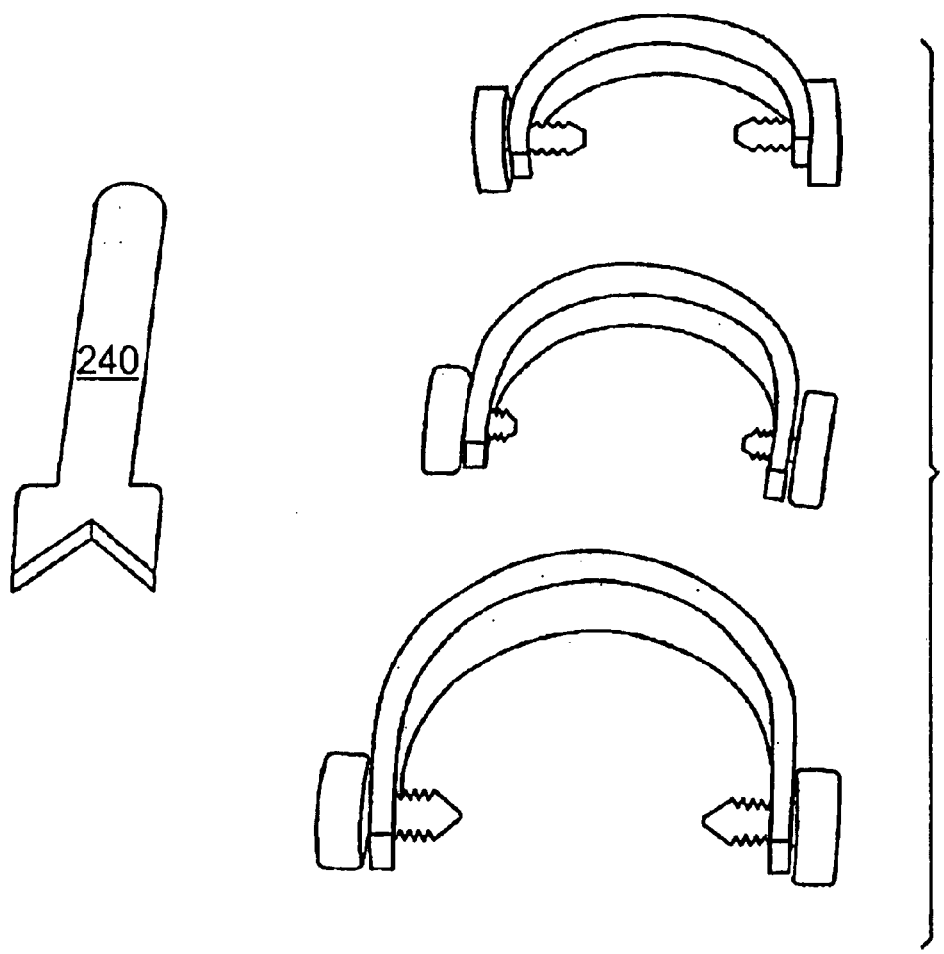
Figure 24B:
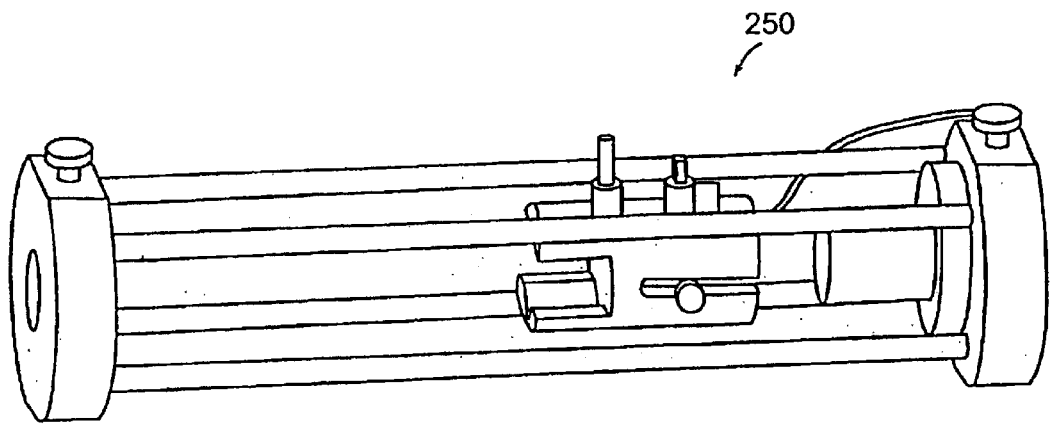
Figure 24C:
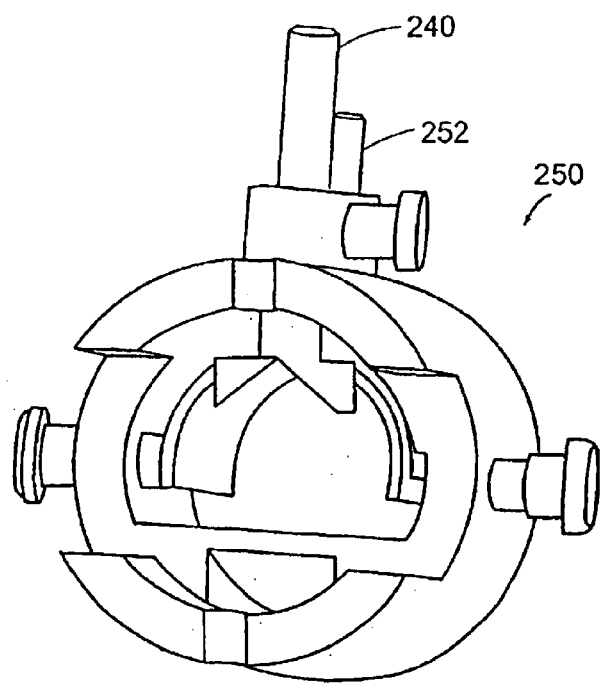

FIG. 24A shows a nose clamp 240 and different size ear caps for rodents. FIG. 24B shows the head restrainer 250 mounted within the support from described previously. FIG. 24C and 24D show a head restrainer 250 that can be used with a rodent, for example, with the nose clamp 240 extending to the bite bar. These figures also show the dome coil 252 of FIG. 17A mounted with the head restrainer.

The following are examples of the use of the apparatus for various applications.

The first example uses magnetic resonance imaging with T2* weighted technique to identify the site and neuropathology of acute intracranial hemorrhage. T2* weighted technique is used to image the onset and progression of a spontaneous hemorrhagic stroke in conscious rats. This allows researchers to have an animal model and method using MRI according to this invention to study the physiology of hemorrhagic stroke in real-time.

MRI data were acquired using a Bruker Biospec DBX 4.7/40 (4.7 Tesla, 40 cm bore Bruker Medical, Inc., Billerica, Mass.) animal MRI/MRS spectrometer using a 15 cm actively shielded gradient inset. Animals between the ages of 12–14 weeks were lightly anesthetized with sodium pentobarbital (25 mg/kg) and fit into the restraining assembly 36 according to the invention. The tail vein was catheterized for the injection of norepinephrine. Functional imaging began no less than 90 min after recovery from anesthesia.

At the beginning of each session, a fast scout (GEFI) imaging sequence of three orthogonal views was used to make sure of the brain orientation. Afterwards, a high quality, proton weighted, spin echo anatomical data set was collected with the following parameters: isotropic 4.8 cm FOV and 256 matrix, 0.187 mm pixel, TR 2000, TE=31 msec, 18 slices, 8.5 minute imaging time. Functional images were obtained using an interleaved T2*-weighted EPI spin echo sequence (256×256, using 16 interleaves) with the same spatial parameters and resolution, but with ten slices, TR=1800, TE=48 msec. The ten coronal slices were acquired every 30 seconds. The sequence was repeated 24 times for a total of 240 images. The first 10 repetitions were baseline data followed by norepinephrine injection.

Figure 25:
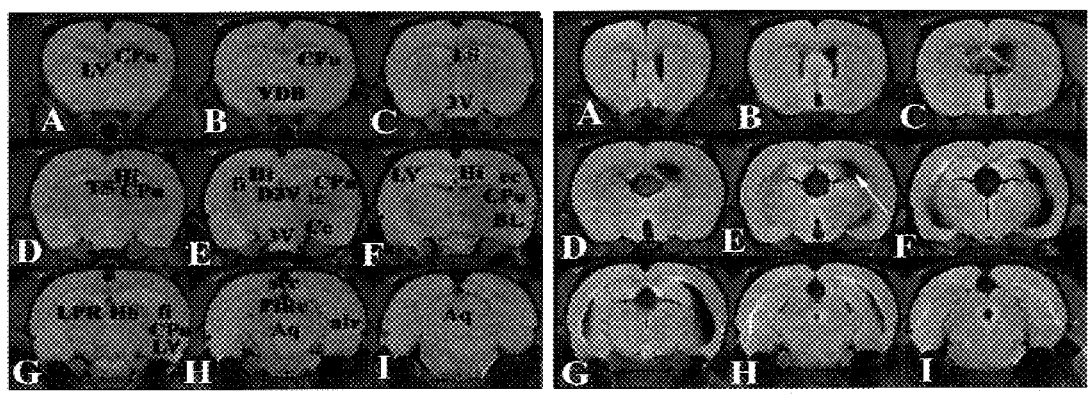
FIG. 25 shows nine contiguous anatomical sections take prior to and sixty minutes following hemorrhagic stroke.

The results of the proton weighted images is discussed followed by the T2* weighted images. Nine contiguous anatomical sections taken prior to and sixty-min following hemorrhagic stroke are shown in FIG. 25. Intracranial hemorrhage caused a dramatic change in proton weighted image contrast. The most obvious morphological change is the exaggerated expansion of the ventricular system highlighted by hypointense signal. In contrast, the parenchyma adjacent to the ventricles is hyperintense. Indeed, one hr after hemorrhagic stroke, the brain shows greater MR signal throughout the parenchyma as compared to the pre stroke condition. From these data it would appear that the stroke occurred in the dorsomedial caudate/putamen adjacent to the lateral ventricle and corpus callosum as shown in FIG. 25, section E.

Figure 26:
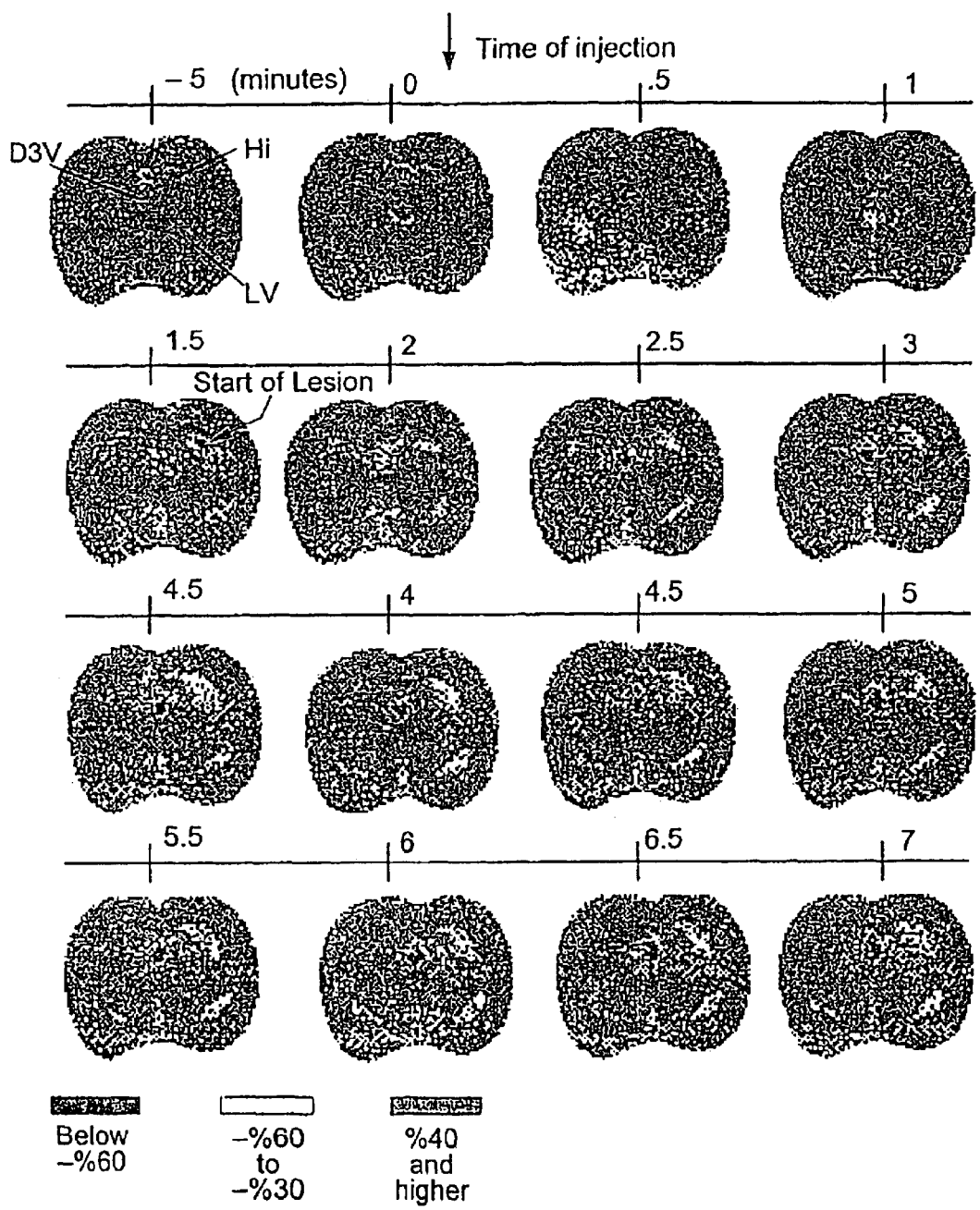
FIG. 26 shows images collected at 30 second intervals over an 8 minute period showing changes in BOLD signal with hemorrhagic stroke in a conscious animal.

Images collected at 30 second intervals over an 8 minute period showing changes in BOLD signal with hemorrhagic stroke in a conscious animal are presented in FIG. 26. Stroke was precipitated by the tail vein injection of a hypertensive dose of norepinephine given during data acquisition. The data presented are from the coronal section shown in FIG. 25, section E. Positive (red voxels) and negative (yellow and black voxels) changes in BOLD signal are mapped over the raw data image. Data from a SPSH rat that did not stroke in response to the tail-vein injection of norepinephrine is shown in FIG. 27.

Thirty seconds after injection of norepinephrine there was a robust increase in BOLD signal over the cerebral cortex in the stroke animal. This increase was accompanied by an equally robust but opposite decrease in BOLD signal in the basal areas of the brain, particularly in the contralateral amygdaloid complex, piriform and perirhinal cortices. These changes in BOLD signal in the first 30 sec following norepinephrine injection corresponds in time with the peak change in blood pressure observed in studies outside the magnet. By one min the decreased BOLD signal was primarily confined to midline thalamic nuclei, while enhanced BOLD signal was more widely but diffusely spread around the brain. Between 60–90 sec after injection there is a decrease in BOLD signal in excess of 60% (black voxels) that appears at the dorsomedial caudate/putamen and third ventricle. The caudate/putamen is the putative site of intracranial hemorrhage. There appears to be a unilateral increase in BOLD signal throughout the striatum on the side of the stroke. Over the course of the next five-min most of the changes in BOLD signal are lateralized to the side of the stroke. However, the amygdaloid complex and piriform cortex shows bilateral activity. Over the course of the study, the striatum expands into a larger area of decreased BOLD signal adjacent to voxels showing increased BOLD signal. This checkerboard pattern where one voxel shows increase in BOLD signal and its adjacent voxel shows decrease in signal is more prevalent as the stroke progresses. The animal was removed from the magnet following the collection of the last proton weighted data set (FIG. 25) approximately 60 min after the initiation of stroke. The animal was conscious and showed normal motor activity when returned to its home cage. However, over the next ninety min the animal's conditioned deteriorated leading to death. Gross histology revealed clotted blood throughout the subarachnoid space over the cerebral hemispheres. The ventricles were distended and filled with blood.

Figure 27:
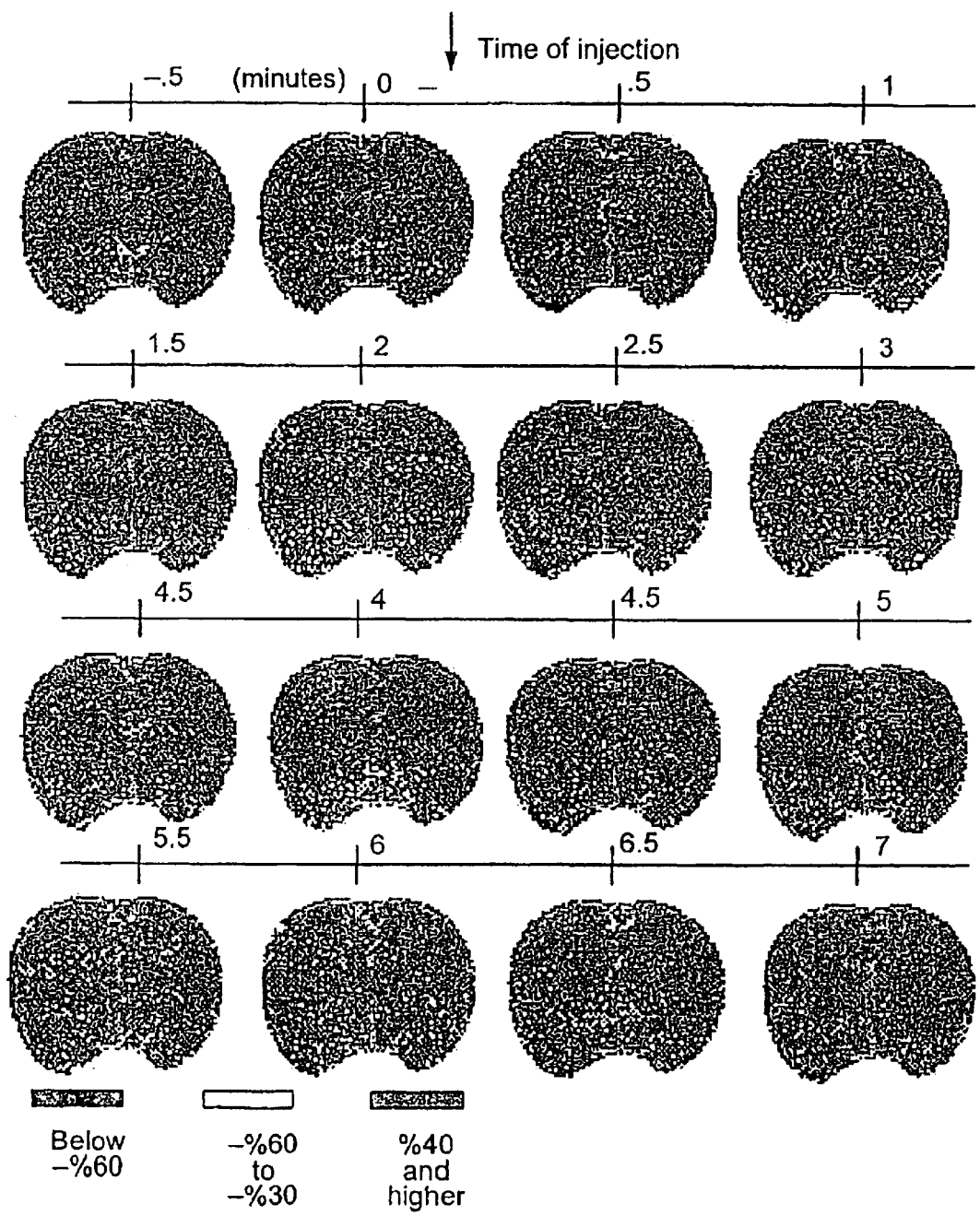
FIG. 27 shows images collected at 30 second intervals over an 8 minute period showing changes in BOLD signal for a non-stroke conscious animal.

A time series at approximately the same coronal plain in a SPSH rat that did not stroke following injection of norepinephrine is shown in FIG. 27. Similar data were collected for the other two animals that failed to stroke during imaging. The cortices and basal ganglia showed no ostensible changes in BOLD signal during the 3–4 min hypertensive episode following injection of norepinephrine. The hypothalamus, particularly the paraventricular and supraoptic nuclei of the hypothalamus showed a sustained increase in BOLD signal. There were no localized, sustained hypointense signals that would indicate intracranial bleeding. This was confirmed by subsequent immunostaining for fibrinogen that revealed no signs of vascular hemorrhage.

The following example relates to using high field MRI to study cocaine addiction in monkeys. Changes in functional activity are observed during cocaine self-administration, withdrawal and reinstatement, i.e., "craving" elicited by the presentation of conditioned cues during magnetic resonance imaging (MRI) in conscious rhesus monkeys. With MRI it is possible to follow brain development, function and chemistry of non-human primates over their lifetime with exceptional spatial and temporal resolution. Therein allowing non-invasive developmental studies to identify changes in neural circuits involved in drug addiction, extinction and reinstatement.

The restraining assembly 36 was sized to fit a 4 kg rhesus (young adult) into a operant/restrainer designed for a 24 cm tunnel bore 212 of an MRI device 210. The restraining assembly 36 with RF electronics including the volume coil 32 and the dome shaped surface coil 196 discussed above is used with a train rhesus monkeys to self-administer cocaine during imaging in a 9.4 T spectrometer.

The rhesus monkeys are habituated for 6–8 wk to the operant/restrainer in a simulated "magnet" environment. Under general anesthesia, animals are implanted with chronic intravenous catheters. Over the following three months, animals are trained to self-administer cocaine to a second order fixed interval schedule in the operant/restrainer in the simulated environment. Prior to imaging, animals are habituated for two weeks to the movement and placement of the restrainer into the magnet. Actually imaging is begun when animals show the same level of cocaine administration in the magnet as they do outside. The animals are imaged during three separate trials (days) of cocaine-self administration. These daily trials characterize the direct pharmacological effects of cocaine for comparison with extinction and reinstatement effects. Extinction trials follow self-administration. Over several days, animals bar press for the injection of saline without the conditioned stimulus (red light). This extinction protocol takes about one week and leads to the diminution of bar pressing. Animals are imaged each day of extinction trials. Presentation of the conditioned stimulus is reinstate bar pressing, a situation analogous to cocaine craving. Reinstatement behavior is most pronounced during the first 2–3 daily trials but quickly wanes thereafter. Animals are imaged during each daily reinstatement trial.

This example is done with the background that cocaine addiction is a national health problem with over three million cocaine abusers in need of treatment. Cocaine addition can take years to develop following first exposure and many more to treat. While the physiological effects of cocaine withdrawal are not as apparent as those for alcohol and barbiturates there is a pattern of symptoms characteristic of cocaine abstinence. Immediately after cessation of drug use there is "crash" of mood with behavioral symptoms of depression, agitation, anxiety and cocaine craving. This period is followed by several weeks of withdrawal characterized by prolonged dysphoria and intense cocaine craving associated with memories of drug-induced euphoria. This period of withdrawal is particularly sensitive to environmental stimuli that the addict associates with drug use. These environmental stimuli or conditioned cues intensify cocaine craving. Following withdrawal, there is lasting cocaine abstinence or extinction. However, conditioned cues can still elicit cocaine craving many years after the last cocaine use and trigger a relapse into drug abuse. A key to understanding cocaine relapse is identifying neural pathways in the brain contributing to cue-evoked craving.

Although cocaine abuse is a human problem, many of the questions involving the neurobiological mechanisms contributing to craving and relapse are more easily studied and manipulated in non-human primates. Indeed, squirrel monkeys and more recently rhesus monkeys have been used for many years to study cocaine abuse. These animals can readily be trained to self-administer cocaine in a classical conditioning paradigm making them amenable to studying cocaine reinforcement, extinction and conditioned reinstatement (craving is a term applied to humans while reinstatement is a more objective term applied to animals). Similar prospective studies establishing addiction, extinction and craving are not possible in human subjects. The problems of spatial resolution, motion artifact and prospective experimental designs are resolved by imaging awake monkeys at ultra-high magnetic field strengths in restraining assembly 36 of the invention. Indeed, functional imaging in non-human primates with a 9.4 T MR spectrometer provides a spatial resolution of 2 mm$^3$ with multi-slice acquisitions in seconds. This level of anatomical resolution with temporal windows of seconds would allow the sequential activation of neural circuits associated with self-administration, extinction and reinstatement in exquisite detail.

A less powerful system would not work. For example, the amygdala an area identified in cocaine craving has over twenty different nuclei and subnuclei 18, 67 that can be divided into the corticomedial and basolateral areas. The nuclei associated with the basolateral amygdala are involved in avoidance learning, stimulus-reward associations and processing of temporal and sequential information. Many of these areas have anatomical boundaries of mm$^3$ or less and would not be resolved in a 1.5 T spectrometer or even in the newer 3.0 and 4.0 T systems.

While work on this example is not complete as a filing, it is expected that it will characterize changes in CNS activity during intravenous cocaine self-administration in rhesus monkeys. In addition, experiments will investigate the ability of environmental stimuli associated with drug-administration to alter CNS function in the absence of cocaine. It is anticipated that presentation of drug-paired stimuli in the absence of cocaine administration will induce a pattern of activation that differs from that induced directly by cocaine. The activation of paralimbic and limbic structures associated with learning and emotion appear critical for cocaine craving and relapse triggered by environmental cues. Understanding the activation and integration of these neural pathways in cue-elicited craving may help in the design of therapeutics and potential psychosocial intervention strategies. Functional MRI in ultra-high magnetic field strengths is non-invasive and provides superior spatial and temporal resolution using the apparatus and method of this invention will help identify discrete nuclei within brain regions postulated to be involved in cocaine abuse.

Any minor head movement can distort the image and may also create a change in signal intensity that can be mistaken for stimulus-associated changes in brain activity. In addition to head movement, motion outside the field of view can also obscure or mimic the signal from neuronal activation. Unfortunately, the use of anesthesia precludes any studies that require emotional and cognitive activities. For example, it would not be possible to study the emotional and cognitive components contributing to cue-induced reinstatement of cocaine self-administration in monkeys. The multi-cylindrical, dual-coil animal restrainer 30 reduces motion artifact while still allowing the use of a non-anesthetized animal.

With the monkey under light ketamine anesthesia, the animal is fit into the head restraining unit 40 with a built in surface coil 34. The plastic semicircular headpiece 262 with blunted ear supports that fit into the ear canals is position over the ears, similar to that shown in FIGS. 18 and 19 with the rat. The head 264 is placed into the cylindrical head holder with the animal's canines secured over a bite bar 108 and ears positioned inside the head holder with adjustable screws, the lateral ear clamping screw 114, fitted into lateral slots 112. The head holder 94 is secured to a center post, the position tube 64, at the front of the chassis and secured to the front-end mounting plate 64. In this design it is easier for the researcher to position the head of the animal into the head restrainer before connecting to the chassis. The body of the animal is placed into the body tube 74. The body tube 74 "floats" down the center of the chassis connecting at the front and rear-end plates and buffered by rubber gaskets. As indicated above, the restraining assembly 36 isolates all of the body movement from the head restrainer unit 40 and RF electronics and minimizes motion artifact. The body restraining unit 42 including the body tube 74 is designed to allow for unrestricted respiration with minimal movement. Once the animal is positioned in the body restraining unit 42, the volume coil 32 is slide over the head restrainer unit 40 and locked into place.

The volume coil 32, the surface coil 34 and head restrainer unit 40 for the rhesus monkey in a 24 cm bore gradient set are similar to those discussed above. The volume oil 32 has in one embodiment 16 elements in contrast to the 12 elements discussed above.

It is recognized that the monkeys need to be acclimated to immobilization stress. The stress caused by immobilization and noise from the MR scanner during functional imaging in fully conscious animals is a major concern. While motion artifact has been eliminated or minimized with animal restraining devices, the confounding variable of stress would at first glance limit the number of experimental applications and cloud the interpretation of data. As animals can be adapted to the imaging procedure as measured by basal levels of stress hormones and resting levels of autonomic activity, then it is possible to isolate the stress-mediated changes in brain activity from those of interest.

Step 1. A prototype two-part chassis is constructed of nylon to fit into the 24 cm bore of the gradient set. This basic two-part system has the advantage of separating the head restrainer and RF electronics from the rest of the body restrainer minimizing motion artifact caused by body movement. A lightly anesthetized rhesus monkey is placed into the body restrainer with its head secured into the head holder containing the phase array surface coil. This unit is connected with two screw rods into the front chassis. The head restrainer is locked into a support post on the front chassis. The TEM volume coil slides along rails extending from the front chassis and positioned surrounding the head restrainer. Once positioned in the magnet the two screw rods will be backed off freeing and isolating the front and back components.

Step 2. Three young adult rhesus monkeys (4.0 to 5.0 kg) are anesthetized with ketamine and used for head and body measurements. The dimensions of the head will determine the minimum internal diameter of the head holder on which the surface and volume coils must be adapted. The distance of the external auditory meatus to the surface of the skull is measured to determine the position of the adjustable screws in the lateral sleeves along the circumference of the head restrainer. This is necessary to position the head in the center of the restrainer. A fully prone position, i.e. animal lying on its stomach, was tested in marmosets and found to be acceptable for fMRI in awake monkeys.

Step 3. The head and body restrainers are fitted into supports that can be screwed into the front and back plates. The body supports have rubber gaskets at their contact with the plates to help isolate any body movement.

Step 4. Male rhesus monkeys (4–5 kg) are examined under imaging conditions as described above. Animals are lightly anesthetized with ketamine and fitted into the head and body restrainer. When fully conscious as measured by eye reflexes and vocalization (ca. 45–60 after the injection of ketamine) saliva is collected. The animal holder slides into a large opaque tube having the bore dimensions of the magnet. After thirty minutes another sample of saliva is collected. The two samples of saliva are assayed for cortisol to evaluate adaptation to the stress of immobilization. This repeated each day for several days and throughout the training period. If salivary cortisol does not return to basal levels then adjustments can be made in the restraining device to reduce the immobilization stress.

Appropriate RF volume coils can be used for anatomical and functional imaging of rhesus monkeys. The system scaleable to accommodate differences in head size of these monkeys. The designs can be utilized for uniform imaging of the whole animal head, or they can be used to generate a uniform transmit field for high sensitivity reception from local regions of interest a phased array surface coils. The systems can be efficiently tuned to one, two or three frequencies as desired, and to the highest frequencies for the desired speed.

Two criteria are sought in a preferred coil for high field animal imaging. First, the coil must be as efficient as possible. Transmision efficiency minimizes RF losses to heat and noise in the monkey. Reception efficiency from a desired field-of-view (FOV), maximizes the SNR. In imaging, spatial and temporal resolutions are proportional to SNR.

This third example relates to the functional neuroanatomy of seizures. Using the apparatus and method described above, the moment-to moment changes in brain activity are examined to gain a greater understanding of the neuronal networks for seizures. Functional magnetic resonance imaging (fMRI), as described above, is used to map brain activity with high spatial and temporal resolution in conscious animals. Functional magnetic resonance imaging is sensitive to changes in the ratio of oxygenated and deoxygenated hemoglobin present in the tissue. These changes are termed blood oxygenation-level-dependent (BOLD) and an enhanced signal reflects an increase in neuronal activity. In this example it was shown robust lateralized increases and decreases in BOLD signal throughout the brain following pentylenetetrazole administration at a dose that routinely causes generalized seizure.

Epilepsies are disorders of neuronal excitability characterized by the repetition of seizures. Identifying the sites in the brain involved in the initiation of seizure activity, its propagation and generalization is an important step towards a better understanding of epileptic disorders. Seizures can be induced by administration of chemical convulsants in normal animals; thus, administration of pentylenetetrazole (PTZ) in rodents elicits various types of generalized seizures including tonic-clonic seizures. This example provides enhanced temporal resolution by using functional magnetic resonance imaging (fMRI) in awake rats to further investigate the neuronal networks involved in PTZ-induced seizure.

Functional MRI using the BOLD technique is sensitive to changes in proton-signal intensity in tissues surrounding blood vessels. The level of paramagnetic deoxygenated hemoglobin in the blood vessels alters the magnetic-susceptibility of the protons flipped by a radiofrequency pulse. Increases in deoxygenated hemoglobin dephase proton spins, shorten T2 relaxation time, and decrease signal intensity. Increased neuronal activity is accompanied by an increase in metabolism concomitant with changes in cerebral blood flow and volume to the area of activation. The local blood flow exceeds oxygen uptake lowering the level of deoxygenated hemoglobin and increasing T2 relaxation time and signal intensity. With ultra high field magnetic resonance imaging and multislice gradient echo pulse sequencing it is possible to follow changes in BOLD signal over much of the brain with high temporal and spatial resolution.

Sprague-Dawley rats (350–400 g) were separated into control and experimental groups. All animals were lightly anesthetized with sodium pentobarbital (25 mg/kg; i.p.). A catheter of 20 gauge polyethylene was inserted into the abdomen and held in place with surgical glue in order to perform intra peritoneal injection. Animals were fitted into a restraining assembly 36, describe above, while control animals were placed in a small cage outside the magnet within the shielded room. After recovery from anesthesia, ca. 90 min, experimental animals were imaged in a 4.7 T Bruker spectrometer using gradient-echo pulse sequence (TR: 146 ms; TE: 20 ms; flip angle: 300; data matrix: 128×128; filed of view: 6.4 cm, pixel size: 0.5 mm; thickness: 1 mm). Images were obtained at 18 sec intervals for over a 16 min period. For each experiment, baseline data were collected over the first 2 min interval, followed by 3 min of data in response to the vehicle (0.9%NaCl) injection. Five min from the start of data collection animals were injected with PTZ at the dose of 50 mg/kg. Since it is not possible to observe PTZ convulsive seizures in animals restrained for imaging, the control group was tested for PTZ seizure susceptibility. These animals received the PTZ injection at the same time as the experimental animals. In control animals, PTZ seizures consisted of brief myoclonus jerks that evolve to forelimb clonus followed by generalized tonic-clonic activity with loss of posture. The first generalized tonic-clonic seizure occurred about 2 min following PTZ injection, and 2–4 seizural episodes were recorded during the next 5–10 min.

Figure 28:
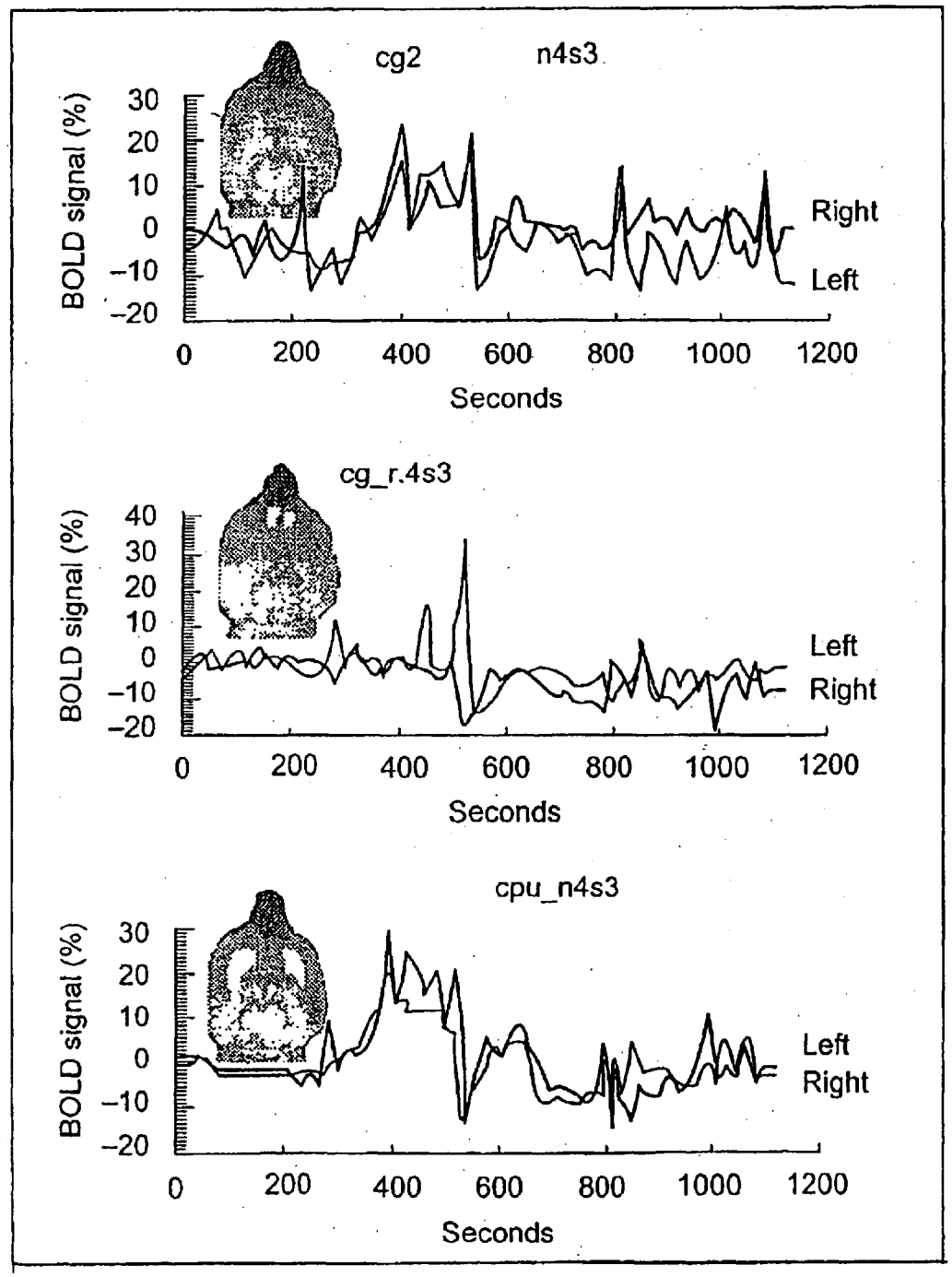
FIG. 28 shows a sequence of graphical illustration of BOLD signal as a function of time.

An example of activational maps for a single animal before and after pentylenetetrazole (PTZ) injection are shown in FIG. 28. These data were obtained by averaging six baseline data sets for each brain section and performing a voxel-by-voxel subtraction of subsequent data sets. Red and yellow areas denote changes in BOLD signal above and below baseline by five standard deviations. These activational maps were overlaid on high resolution anatomical maps collected at the same brain slice thus, providing accurate anatomical identification.

There was no change in BOLD signal following injection. Within 60 sec after PTZ injection there was significant change in signal mainly in corticolimbic areas that favored laterization to the left parietal and temporal cortices. The first convulsive seizure occurred in the control animal at approximately 90 sec after PTZ injection. Activational maps at this time showed a polarity and lateralization between increased and decreased BOLD signal covering large areas of the brain, particularly the cortex. In the data set immediately afterwards, the enhanced BOLD signal in left cortical areas persists while the decrease in BOLD signal in other sites abates.

Changes before the occurrence of seizures, increased levels in BOLD signal was found in an number of cortical sites including entorhinal, insular, perirhinal, parietal and temporal cortex as well as in the hippocampus formation. During PTZ seizures, BOLD activation exhibited a laterialized pattern. Thus, increased levels in BOLD signal was greater in the cerebral hemisphere that exhibited an earlier neuronal activation (BOLD signal) following PTZ injection. The increased levels in BOLD signal were mainly observed in cortical sites including perirhinal, insular, parietal, occipital and temporal cortex. No increased levels in BOLD signal were observed in the frontal cortex during PTZ seizures. In this example, BOLD signal was initially observed in the cortex in the left cerebral hemisphere following PTZ injection. This unilateral pattern of BOLD signal was greater during PTZ seizures. In contrast, no increased levels in BOLD signal was found in the right cerebral hemisphere following PTZ injection. Only few structures were activated during PTZ seizures in the right cerebral hemisphere.

Changes in BOLD signal over time were also examined in a number of CNS sites. Among cortical sites, the dramatic BOLD activation was observed in the entorhinal cortex. Indeed, increased levels in BOLD signal occurred immediately before PTZ seizures in the entorhinal cortex in the left cerebral hemisphere, as compared to the one in the right hemisphere. BOLD signal increases in the entorhinal cortex were sustained over 12 min following PTZ seizures. Note that is this example the increased levels in BOLD signal was greater in the left cerebral hemisphere. The perirhinal, piriform, parietal and temporal cortex only exhibited a transient increased levels in BOLD signal concomitantly to the occurrence of PTZ seizures. Like the entorhinal cortex, the olfactory bulb also exhibited a sustained increased in BOLD signal. Although BOLD signal was increased in the hippocampal formation in both cerebral hemisphere, a unilateral pattern could be observed during PTZ seizures. Thus, changes in BOLD signal in the left and right hippocampal formation was sustained during 12 and 6 min, respectively. A sustained increased levels in BOLD signal was also observed in both left and right substantia nigra. Only modest and sporadic increased levels in BOLD signal was observed in both left and right striatum, as well as in the septum and superior colliculi. No changes in BOLD signal was found in the thalamus and in the inferior colliculi.

Neuronal depression was also examined. In control, no neuronal depression was observed. Immediately before PTZ seizures, neuronal depression was only observed in few CNS sites including cortex (frontal, perirhinal, piriform, insular parietal, occipital and temporal), striatum and colliculi. However, a massive neuronal depression was observed during PTZ seizures, and was primarily localized in the contralateral cerebral hemisphere that did not exhibit increased levels in BOLD signal. Neuronal depression was observed in cortical sites (forebrain (striatum, septum, thalamus, hippocampus formation) and brainstem (colliculi) sites as well as the cerebellum during seizures. During recovery from PTZ seizures, only few brain sites exhibited neuronal depression.

The early increase in BOLD signal in cortical sites was dramatically increased during convulsive seizure. Thus, the cortex is critical for the pre-ictal and ictal phases of generalized seizure. Unfortunately, in these studies the amygdala was obscured because of the susceptibility problems associated with T2* imaging around air-filled sinuses. Hence it was not possible to evaluate the contribution of this important limbic area in seizure initiation and propagation.

This example demonstrates that fMRI is useful to examine the propagation seizure activity in conscious animals. This technique revealed the spatiotemporal pattern of spreading BOLD, allowing identification of the site of onset of seizure activity and its propagation. No dissociation between clonic and tonic network. This example further demonstrates that it is possible to map neuronal activity-related signal associated with convulsions in conscious animal using fMRI.

Figure 29A:
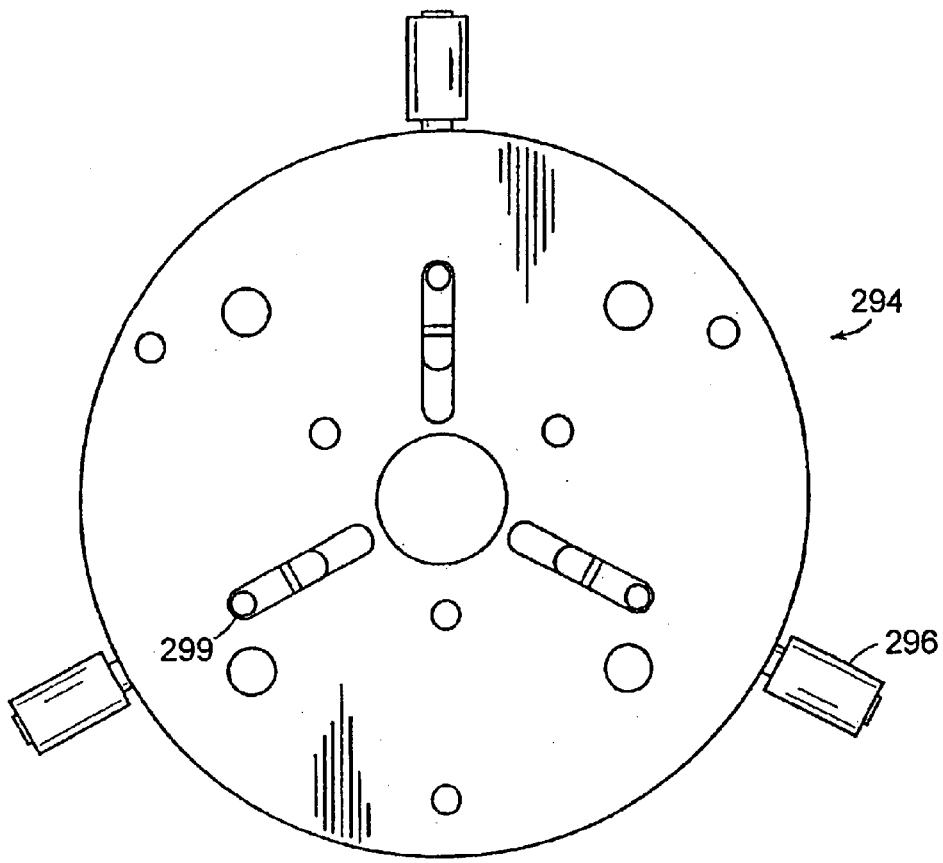
FIGS. 29A and 29B are front and side perspective views of an adjustable embodiment of the front-end mounting plate.
Figure 29B:
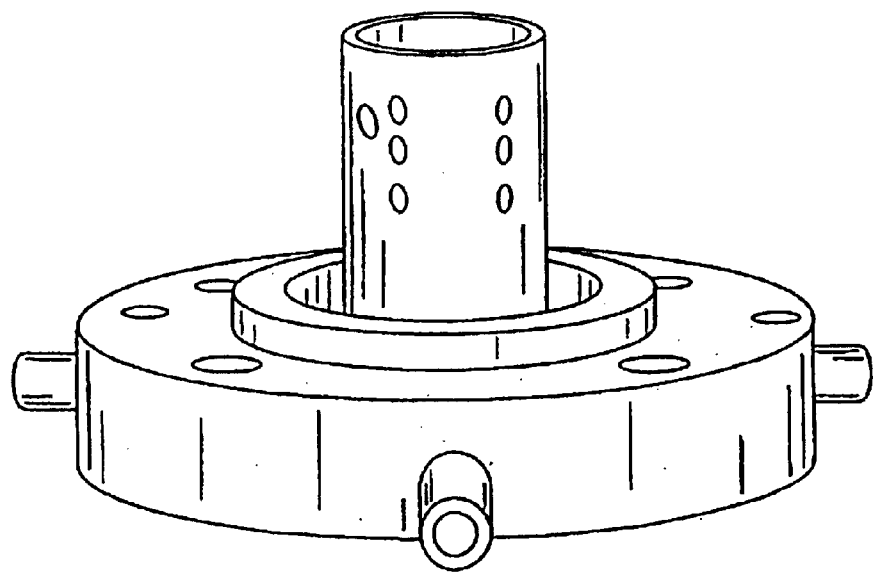
Figure 30:
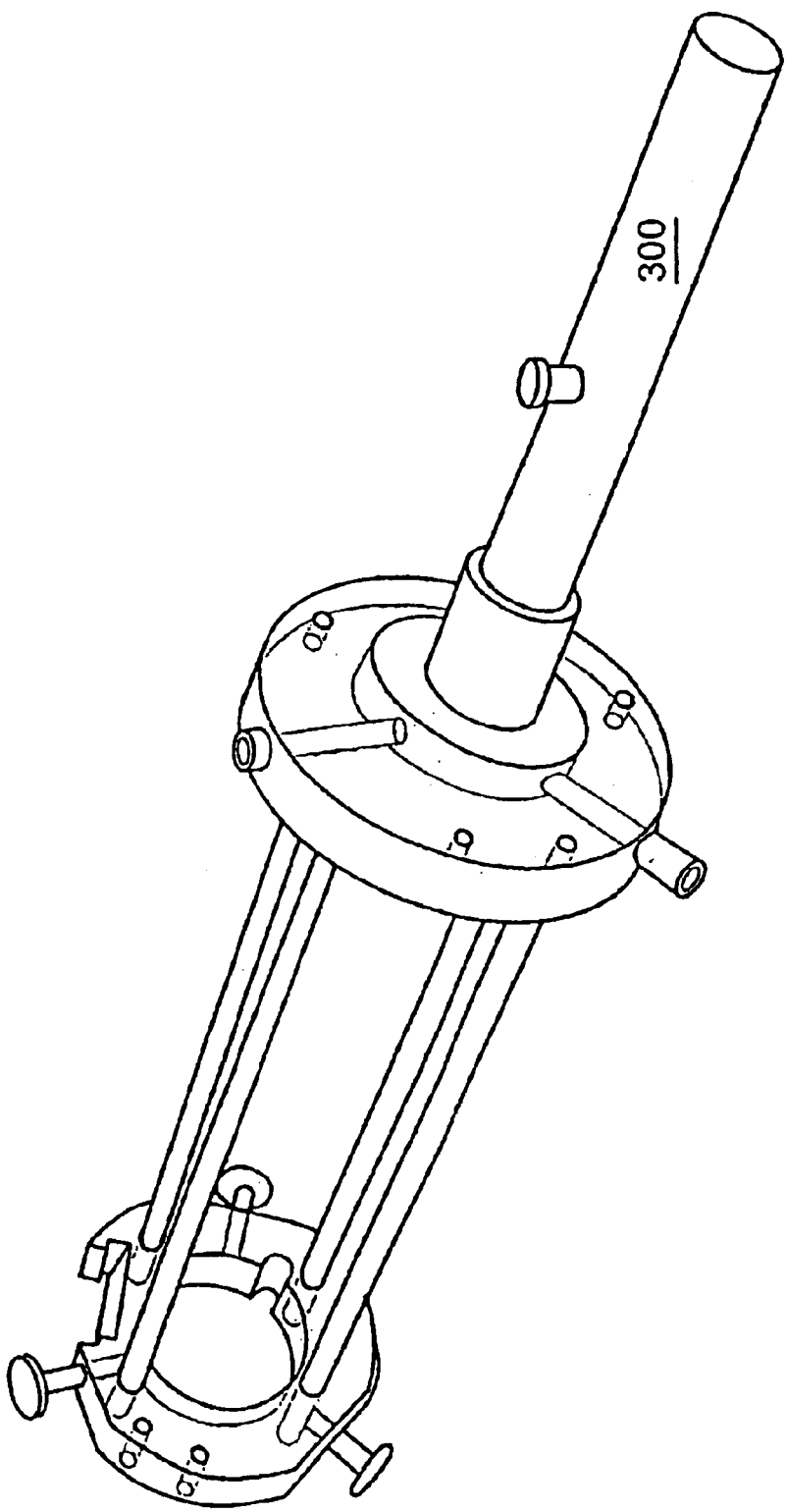
FIG. 30 is a perspective view of the adjustable mounting assembly.

Referring to FIGS. 29A and 29B, an alternative front-end mounting plate 294 is shown. The front-end mounting plate 294 has a plurality of projecting mounting rods 296 for engaging the surface of the tunnel bore 212. The mounting rods 296 are slideably received in bores in the front-end mounting plate 294. The mounting rods 296 have a bias mechanism, such as an elastic received on a protrusion 299 of each rod to retract the mounting rods. An adjustment handle 300 shown in FIG. 30 is positioned in the hole has an adjustment mechanism, such a tapered shape that moves along the frame axis, to force the mounting rods 296 outward.

The present invention demonstrates novel images of neuronal activation in conscious animals. Current methods utilizing anesthetized animals, which are known to exhibit dampened neuronal activity, may mask low signal levels. Furthermore, since the level of arousal (conscious vs. anesthetized) is inextricably linked to behavior, the future use of this assembly will be a significant step in providing a better understanding of the neural circuitry that facilitates behaviors such as responses to visual stimulation, temperature regulation, and motor stimulation, in addition to a range of different environmental stressors and develop mental and intraneurodevelopmental studies. Therefore, researchers interested in the brain and/or behavior (utilizing laboratory animals) will be further assisted in their analysis of the efficacy of medications, with the utilization of this assembly.

While this invention has been particularly shown and described with references to preferred embodiments thereof, it will be understood by those skilled in the art that various changes in form and details may be made therein without departing from the scope of the invention encompassed by the appended claims.

What is claimed is:

1. A restraining assembly for an awake animal within a magnetic resonance imaging (MRI) device comprising:
   a head restrainer that restrains a head of an awake animal;
   a body restrainer that holds a body of the awake animal;
   a support frame positioned in a cavity of the MRI device, the support frame carrying the head restrainer and the body restrainer;

a volume coil mounted on the support frame, the volume coil extending around the body restrainer such that the assembly can be inserted in the MRI device, the volume coil surrounding the head restrainer; and an RF surface coil disposed within the an interior of the head restrainer for placement proximate the animal's head.

2. The restraining assembly of claim 1 wherein the head restrainer comprises:

a head holder having a channel that receives and restrains the head, the head holder being disposed within the volume coil and having a surface coil positionable within the volume coil;

a position tube carried by a support mount that retains the head holder, the head holder having an aperture in the position tube, a bite bar within the aperture and a plurality of lateral ear clamping members to secure an animal's head.

3. The restraining assembly of claim 2 wherein the body restrainer comprises:

an elongated body tube carried by a mounting unit; and a shoulder positioning device carried by the elongated body tube that positions the shoulders of the animal.

4. The restraining assembly of claim 1 wherein the frame comprises:

a front mounting plate having an access hole extending through the plate, the front mounting plate adapted to be secured into the bore of the MRI device;

a rear mounting plate parallel and spaced from the front mounting plate and having an access hole extending through the plate, the rear mounting plate adapted to be secured into the bore of the MRI device; and a plurality of support rods extending between the mounting plates to space and support the mounting plates in relative position, the support rods including a damping structure for reducing transmission of movement of the body restrainer to the head retainer.

5. The restraining assembly of claim 4 wherein the damping structure of the frame further comprises gaskets interposed between the support rods and the mounting plates for reducing transmission of movement of the body restrainer to the head restrainer.

6. The restraining assembly of claim 4 wherein the damping structure further comprises a gasket interposed between the front mounting plate and the position tube of the head restrainer for reducing transmission of movement of the body restrainer to the head restrainer.

7. A non-magnetic restraining system to immobilize an awake animal for insertion into a bore of a magnetic resonance imaging (MRI) device comprising:

a support frame adapted to be slidably mounted in the bore of the MRI device, the frame including:

a front mounting plate having an access hole extending through the plate;

a rear mounting plate parallel and spaced from the front mounting plate; and a plurality of support rods extending between the mounting plates to space and support the mounting plates in relative position;

a body restrainer for holding the body of the awake animal, the body restrainer including:

an elongated body tube carried by the frame; and a shoulder restrainer carried by the elongated body tube; and a head restrainer for immobilizing the head of the awake animal, the head restrainer including:

a head holder having an opening to receive and restrain the head of an animal, the head holder receiving an RF surface coil in the opening; and a position tube carried by the frame for retaining the head holder, the head holder having an aperture extending from the opening to communicate with an aperture in the position tube.

8. The restraining assembly of claim 7 further comprising a volume coil to generate an excitation RF signal, the volume coil having a cylindrical non-magnetic core module having an outer shield and a longitudinal axis, a cylindrical bore extending through the core module along the longitudinal axis and defining an inner surface, a plurality of bores extending parallel to, and spaced from, the longitudinal axis, each bore receiving one of the support rods for lateral movement of the volume coil relative to the head restrainer.

9. The restraining system of claim 8 wherein the head holder further comprises a pair of lateral ear clamping screws extending horizontally through the sides of the head holder into the bore of the aperture and perpendicular to the axis and above a horizontal bite bar to abut and limit the horizontal movement of the animal.

10. The restraining system of claim 9 wherein the head holder further comprises a nose clamping screw extending inward through the top of the head holder into the bore of the aperture that abuts the nose of an animal above the bite bar and secures the animal's jaw thereon.

11. The restraining system of claim 9 wherein the head holder further comprises a pair of jaw anchor screws extending inward through the head holder into the bore of the aperture and a head clamping screw located at the top of the head holder and extending inward through the head holder into the bore of the aperture.

12. The restraining system of claim 9 further comprising a restraining jacket that restrains the body of the animal.

13. The restraining system of claim 12 wherein the head holder further comprises a nose clamping screw extending inward through the top of the head holder into the bore of the aperture and adapted to abut the nose of an animal above the bite bar and secure the animal's jaw thereon.

14. The restraining system of claim 13 wherein the head holder further comprises a pair of jaw anchor screws extending inward through the head holder into the bore of the aperture.

15. The restraining system of claim 14 further comprising ear pads wherein the ear pads are placed under a protective ear piece.

16. The restraining system of claim 15 wherein the head holder further comprises a head clamping screw located at the top of the head holder and extending inward through the head holder into the bore of the aperture.

17. The restraining system of claim 8 wherein the RF surface coil detects the MRI signal and is carried by the head holder.

18. The restraining system of claim 17 wherein the volume coil further comprises:

a plurality of conductive strip lines, the strip lines extending parallel to the longitudinal axis on the inner surface of the core module;

a pair of circuit boards carried by the ends surfaces of the core module;

a plurality of shielding strips extending parallel to the longitudinal axis on the outer surface;

a resonating element having strip lines, a shielding strip, and at least one tuneable, variable capacitor;

a detuning circuit carried on the circuit board for detuning the resonating element; and a RF decoupling circuit carried on the circuit boards for reducing interference between a DC detuning signal and an RF signal.

19. The retraining system of claim 18 further comprising a transceiver unit having a RF transmitter and a RF receiver, the transceiver unit connected to the surface coil and the volume coil.

20. A volume coil for a magnetic resonance system, the volume coil comprising:

a cylindrical non-magnetic core module having an outer surface and a longitudinal axis, a cylindrical bore extending through the core module along the longitudinal axis and defining an inner surface;

a plurality of conductive strip lines fixedly attached to the inner surface of the core module, the strip lines extending parallel to the longitudinal axis of the core module;

a pair of circuit boards carried by the ends of the core module;

a plurality of shielding strips extending parallel to the longitudinal axis on the outer surface of the core module;

a resonating element having strip lines, shielding strips and at least one tuneable capacitor;

a detuning circuit formed as part of the circuit board for detuning the resonating element; and an RF decoupling circuit formed as part of the circuit board for reducing interference between a DC detuning signal and an RF signal.

21. The volume coil of claim 20 wherein the core module is formed of Teflon or nylon.

22. The volume coil of claim 20 wherein the strip lines are electroplated on the core module.

23. The volume coil of claim 20 wherein the adjacent shielding strips are coupled by at least one capacitor attaching adjacent shielding strips at alternative ends of the shielding strips.

24. The volume coil of claim 23 further comprising:

a matching circuit for adjusting the impedance of the resonating elements to that of the RF source and a filter for separating the high frequency RF signal from interfering the DC detuning signal.

25. The volume coil of claim 24 wherein the detuning circuit has a pair of pin diodes.

26. The volume coil of claim 24 wherein the RF decoupling circuit has a plurality of high frequency inductors.

27. A restraining assembly to immobilize an awake animal for insertion into a magnetic resonance imaging (MRI) device, the assembly comprising:

a support frame configured for placement within a bore of the MRI device;

a volume coil slidably displaceable along a longitudinal axis of the support frame;

an elongated body member coupled to the support frame for holding the body of the awake animal;

a head restrainer coupled to the elongated body member such that the volume coil surrounds the head restrainer when the volume coil is in an operating position; and a surface coil adjustably mounted relative to the head restrainer such that the volume coil surrounds the surface coil in the operating position.

28. The assembly of claim 27, wherein the surface coil is received through an aperture formed in the head restrainer so that the surface coil is disposed within an interior of the head restrainer in the operating position.

29. The assembly of claim 27, wherein the frame includes a front mounting plate and a rear mounting plate spaced therefrom and a plurality of support rods extending therebetween, the volume coil having a plurality of complementary bores formed therein to receive the support rods to permit the volume coil to be slidably displaceable relative to the frame.

30. The assembly of claim 27, wherein the head restrainer includes a plurality of restraining features for locating and restraining the head of the animal within the head restrainer so that horizontal movement of the animal is restricted.

31. The assembly of claim 27, wherein the elongated member has a cut-out formed therein for receiving and positioning the head restrainer.

* * * * *